United States Patent
Visvanathan et al.

(10) Patent No.: US 9,924,870 B2
(45) Date of Patent: Mar. 27, 2018

(54) MONITORING PHYSIOLOGICAL PARAMETERS

(71) Applicant: TATA CONSULTANCY SERVICES LIMITED, Mumbai (IN)

(72) Inventors: Aishwarya Visvanathan, Bangalore (IN); Arpan Pal, West Bengal (IN); Anirban Dutta Choudhury, West Bengal (IN); Tanushyam Chattopadhyay, West Bengal (IN); Anurag Kumar, Haryana (IN); Rohan Banerjee, West Bengal (IN); Aniruddha Sinha, West Bengal (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 894 days.

(21) Appl. No.: 14/444,745

(22) Filed: Jul. 28, 2014

(65) Prior Publication Data
US 2015/0031965 A1    Jan. 29, 2015

(30) Foreign Application Priority Data

Jul. 26, 2013 (IN) .......................... 2489MUM2013
Oct. 3, 2013 (IN) .......................... 3152MUM2013
May 2, 2014 (IN) .......................... 1540MUM2014

(51) Int. Cl.
*G06K 9/00* (2006.01)
*A61B 5/00* (2006.01)
(Continued)

(52) U.S. Cl.
CPC .......... *A61B 5/0059* (2013.01); *A61B 5/0205* (2013.01); *A61B 5/02416* (2013.01);
(Continued)

(58) Field of Classification Search
CPC . A61B 5/0059; A61B 5/0205; A61B 5/02416; A61B 5/02438; A61B 5/04028;
(Continued)

(56) References Cited

U.S. PATENT DOCUMENTS 6,540,686 B2 * 4/2003 Heikkila ............ A61B 5/14532
128/925
2009/0226071 A1 9/2009 Schuler et al.
(Continued)

FOREIGN PATENT DOCUMENTS

CN 102429649 A 5/2012
EP 2438849 A1 4/2012

OTHER PUBLICATIONS

Wieringa et al (Contactless Multiple Wavelength Photoplethysmographic Imaging: A first step toward "SpO2 Camera" Technology, Annals of Biomedical Engineering, vol. 33, No. 8, Aug. 2005, pp. 1034-1041).*
(Continued)

*Primary Examiner* — Amara Abdi
(74) *Attorney, Agent, or Firm* — Lee & Hayes, PLLC

(57) ABSTRACT

A method for monitoring physiological parameters associated with a subject using a hand held device is described herein. In an implementation, the method includes obtaining a plurality of sample photoplethysmographic (PPG) features associated with a sample subject, from a video of a body part of the sample subject. From among the plurality of sample PPG features, at least one relevant sample PPG feature associated with the physiological parameter, is selected based on a ground truth value of the physiological parameter for the subject. Further, based on the at least one relevant sample PPG feature and the ground truth value of the physiological parameter, a mathematical model indicative of a correlation between the relevant sample PPG feature and the physiological parameter, is determined. The mathemati-
(Continued)

cal model can be deployed for monitoring the physiological parameter in real time.

47 Claims, 6 Drawing Sheets

(51) Int. Cl.
*A61B 5/0205* (2006.01)
*A61B 5/1455* (2006.01)
*A61B 5/0402* (2006.01)
*A61B 5/024* (2006.01)
*A61B 5/021* (2006.01)
*A61B 5/08* (2006.01)

(52) U.S. Cl.
CPC ...... *A61B 5/02438* (2013.01); *A61B 5/04028* (2013.01); *A61B 5/14551* (2013.01); *A61B 5/7267* (2013.01); *A61B 5/021* (2013.01); *A61B 5/08* (2013.01); *A61B 5/6898* (2013.01); *A61B 2505/07* (2013.01)

(58) Field of Classification Search
CPC .............. A61B 5/14551; A61B 5/7267; A61B 2505/07; A61B 5/021; A61B 5/08; A61B 5/6898

See application file for complete search history.

(56) References Cited

U.S. PATENT DOCUMENTS

| 2009/0326349 | A1 | 12/2009 | McGonigle et al. |
| 2010/0286495 | A1* | 11/2010 | McGonigle .......... A61B 5/0816 600/330 |
| 2011/0190598 | A1* | 8/2011 | Shusterman .......... G06Q 50/22 600/301 |
| 2012/0130201 | A1* | 5/2012 | Jain .......................... A61B 5/08 600/301 |
| 2013/0079649 | A1 | 3/2013 | Mestha et al. |
| 2013/0310660 | A1 | 11/2013 | Zuckerman-Stark et al. |

OTHER PUBLICATIONS

Vikram Chandrasekaran, Measuring Vital Signs Using Smart Phones, Dec. 2010, p. 9, 39, 38, 40, 47, fig. 4.7.
English Translation of CN102429679, Xianglin Yang et al., Continuous blood pressure measuring device, May 2, 2012, 16 pages.
Christopher G. Scully et al., Physiological Parameter Monitoring From Optical Recordings With a Mobile Phone, Jul. 29, 2011, 11 pages.

* cited by examiner

MONITORING PHYSIOLOGICAL PARAMETERS

TECHNICAL FIELD

The present subject matter relates, in general, to measurement of physiological parameters and, particularly but not exclusively, to monitoring physiological parameters using a hand held device.

BACKGROUND

Monitoring of certain physiological parameters and vital signs of a person, such as respiration rate, pulse rate, and blood pressure, may be achieved in a clinical setting. Generally, it has been observed that if a person is aware that his or her physiological parameters are being monitored, it may cause the person to become conscious. Consequently, one or more of the physiological parameters may be reported erroneously. Therefore, several non-invasive techniques for monitoring the physiological parameters have been developed.

One such non-invasive technique is photoplethysmography (PPG). PPG involves an optical methodology, which can be unobtrusive in certain cases, working on the basis of dynamics of blood volume changes in the vasculature under the skin. Conventionally, PPG is implemented in various ways for measuring and monitoring physiological parameters, for example, by contactless recording of videos of the subject whose physiological parameters are to be measured.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
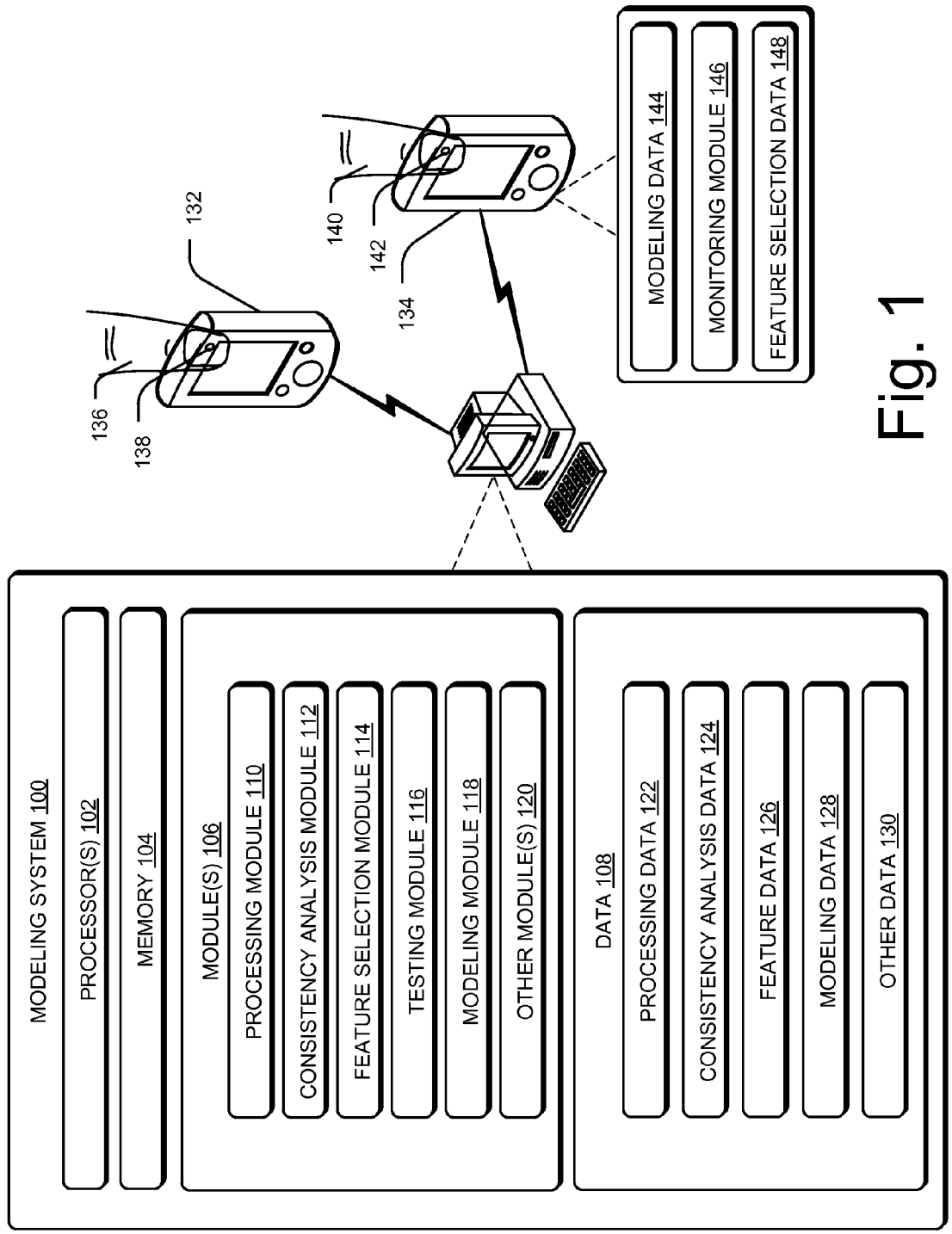
FIG. 1 illustrates a physiological parameter monitoring device coupled to a modeling system for monitoring physiological parameters associated with a subject, in accordance with an implementation of the present subject matter.

The present subject matter relates to monitoring physiological parameters associated with a subject, using a hand held device.

Conventionally, photoplethysmography (PPG) is implemented in various ways for measuring and monitoring physiological parameters. In few conventional techniques, a video of the subject whose physiological parameters are to be measured is captured from a distance and the video is, then, analyzed for determining the physiological parameters. In such techniques, other objects and persons in the field of view may cause the measurement of the physiological parameters to be erroneous. Accordingly, certain other conventional techniques may involve positioning a part of the body of the subject in contact with the camera and, then, using the video for measuring the physiological properties. For measuring the physiological parameters, conventional techniques usually involve a video recording device for recording the video to obtain the PPG waveform. Such techniques, however, involve the subject to be substantially motionless, so that the contact between the subject and the camera is maintained throughout the procedure. In case the subject makes an unwanted movement during measurement of the physiological parameters, say because of shivering or coughing or sneezing, the physiological parameters measured, thereafter, may be erroneous. In addition, the subject is not informed of the defect in capturing of the video or the erroneous measurement of the physiological parameters, and as a result of the erroneous measurement, the subject may be incorrectly diagnosed. Furthermore, the equipment conventionally used for measuring the physiological parameters is bulky and can cause inconvenience for the user in measuring the physiological parameters.

To enhance the accuracy of measurement of the physiological parameters, conventionally, a sensing device, such as a pulse oximeter or a sound-based sensor, say for measuring heart rate, is usually used in conjunction with the video recording device for monitoring the physiological parameters, and characteristics measured by the sensing device are used in combination with the PPG waveform. However, while the measurement of the physiological parameters is considerably accurate with the use of the sensing device in addition to the PPG waveform, the cost associated with the apparatus for monitoring the physiological parameters in such a way is high. Further, the apparatus is not portable and may not be usable for mobile implementations. In addition, the processing and analysis of the PPG waveforms uses large amounts of computational resources and time, rendering the technique cumbersome and time consuming. Therefore, the conventional techniques for measuring the physiological parameters lack accuracy and are computationally resource-intensive.

The present subject matter describes methods and devices to determine physiological parameters associated with a subject using a hand held device. According to an aspect, the present subject matter can be an implementation of photoplethysmographic techniques which involve non-invasive techniques for measuring physiological parameters. The physiological parameters can include, for example, heart or pulse rate, pulse oximetry ($SpO_2$) which indicates blood oxygen level, respiration rate, blood pressure, or heart condition based on an electrocardiograph (ECG) features. In an example, the hand held device can be a smart phone or a tablet personal computer (PC).

The present subject matter involves the determining of physiological parameters with substantial accuracy. For the purpose of accurately determining the physiological parameters, according to an implementation of the present subject matter, a sample video captured for determining the physiological parameters is checked for consistency. Once the sample video is determined to be consistent, a set of relevant sample PPG features are extracted from the sample video, and, based on the relevant sample PPG features and ground truth values of the physiological parameter, a mathematical model is determined. The mathematical model is deployed in a device, such as a hand-held device, for monitoring the physiological parameters in real time. In an example, the relevant sample PPG features can be those features which share a discernible relation with the physiological parameter to be monitored, and are distinguishably indicative of the physiological parameter.

According to an implementation, a video of a body part of the subject is captured using the hand held device, for example, a camera of the hand held device. In said example, the video of the body part is captured while the body part is abutted against a lens of the camera. For instance, a video of a finger tip of the subject can be captured for measuring the physiological parameters. Further, the video is processed to obtain a sample PPG waveform. In one example, the sample PPG waveform can be obtained by processing the video for quantized colour value of each frame in the video, and then determining a frequency of the quantized colour value in each frame in a predetermined set of frames. The sample PPG waveform is then determined based on the frequency of the frames in the set. Further, in one case, a consistency analysis of the sample PPG waveform can be achieved to determine whether the sample PPG waveform is consistent or not, and whether the sample PPG waveform can be used for modeling or not.

In an implementation, the video is processed to obtain a sample PPG waveform. In one example, the sample PPG waveform can be obtained by processing the video for quantized colour value of each frame in the video, and then determining a frequency of the quantized colour value in each frame in a predetermined set of frames. The sample PPG waveform is then determined based on the frequency of the frames in the set. As part of obtaining the sample PPG waveform, a plurality of windows is obtained from the video and each window includes a predetermined number of frames. In an example, the windows can be so obtained that certain frames of one window overlap certain frames of the adjacent windows. As would be understood, the term adjacent as used above is in context to the windows lying on a time axis. Further, a predetermined number of windows, when obtained, are used for consistency analysis of the predetermined number of windows is performed to determine consistency of the video. Subsequently, one or more physiological parameters associated with the subject are determined when the video is determined to be consistent.

In an implementation, while processing and preparing the video for consistency analysis, one or more quantized colour value for each frame in the plurality of windows can be determined. In an example, the quantized colour value can belong to a colour model. Accordingly, in case in which the colour model is the Red-Green-Blue (RGB) colour model, the quantized colour value can be an average value of any one of the red, blue, or green component. In another example, in case the colour model is the Hue-Saturation-Value (HSV) model, the quantized colour value can be an average value of any one of the hue, saturation, or value components of the colour model.

Further, according to said implementation, the quantized colour value for each frame can be compared to a predetermined range of quantized colour values, say to check whether the quantized colour value is within the predetermined range. In case the quantized colour value is within the predetermined range, then it indicates that the captured frames are ineffective for determining the physiological parameters. Accordingly, a feedback, say in the form of a pop-up message on the screen of the hand held device, can be provided to the subject to reposition the camera with reference the body part, or vice-versa, to capture a new video for analysis and for determining the physiological parameters. On the other hand, if the quantized colour value lies outside the predetermined range, then the captured video can be further used for consistency analysis and, subsequently, for determining the physiological parameters.

According to an aspect, the consistency analysis can be performed based on peak frequency of the quantized value of colours in the windows of the video. In an example, a Short-Term Fourier Transform (STFT) can be applied to the quantized colour value of the frames to determine the peak frequencies, for consistency analysis. Employing STFT technique for determining peak frequencies can facilitate in determining the peak frequencies with considerable accuracy. In another example, a Fast Fourier Transform (FFT) technique can be applied to the quantized colour value of the frames to determine the peak frequencies, for consistency analysis. In the above examples, applying the STFT or FFT techniques to the quantized colour values generates the sample PPG waveform.

As mentioned previously, the predetermined number of consistent windows having the quantized colour values within the range is used for consistency analysis. In other words, the consistency analysis can be performed when the predetermined number of windows having quantized colour values of frames within the predetermined range is obtained. Such windows from the plurality of windows for which the quantized values of frames are within the predetermined range are referred to as determinant windows. In an implementation, a position of peak frequency of the quantized colour value for each determinant window can be determined based on the quantized value of colours in the frames of the respective determinant window. For instance, the position of the peak frequencies is determined from the sample PPG waveform for the determinant window. Further, a frequency drift for the peak frequencies across the determinant windows is ascertained. In an example, the frequency drift is indicative of variation in position of peak frequency across the determinant windows. Further, if the frequency drift is beyond a threshold frequency drift, then it indicates that the determinant windows and, therefore, the video, are inconsistent.

In an aspect, in case the frequency drift is within the threshold frequency drift, then another step is performed to check whether the video is consistent or not. Accordingly, in an implementation, a signal amplitude of the quantized colour value, for example, amplitude of the quantized colour value, is determined in each frame in the determinant windows and the signal amplitude is checked against a threshold signal amplitude. The signal amplitude of all the frames being greater than the threshold signal amplitude is indicative of the consistency of the video captured for determining the physiological parameters. In case the captured video is determined to be inconsistent, a feedback can be provided to the subject for capturing a new video.

Once the PPG waveform, or in other words, the video, is determined to be consistent, a plurality of sample PPG features is extracted from the sample PPG waveform. In an example, the sample PPG features can be extracted in time domain; however, in another example, the sample PPG features can be extracted in frequency domain. In yet another example, the sample PPG features can be extracted in the time domain as well as frequency domain. Further, in case the sample PPG features are extracted from the sample PPG waveform in the time domain, the sample PPG features extracted in the time domain, also referred to as time domain features, can include features, such as a peak-to-peak time interval for the peaking frequencies in the sample PPG waveform, pulse interval, crest time indicative of the time taken for the sample PPG waveform to reach the peaking frequencies, diastolic time indicative of a time difference between a peak and a next peak minima, height of the pulse, and area under the sample PPG waveform. Further, in an example, the sample PPG features extracted in the frequency domain, also referred to as frequency domain features, can include location of peak frequency, distance between the dominant peak frequency and the immediate peak frequency, spectral centroid, and width of dominant peak frequency region. According to an example, physical characteristics, such as weight of the subject, height of the subject, and age of the subject, associated with the subject can also be taken into account as some of the sample PPG features.

According to an aspect of the present subject matter, once the sample PPG features have been extracted, a two-step approach is followed for selecting the relevant sample PPG features from the entire set of extracted sample PPG features. In the first step, a correlation between the sample PPG features and actual known values of the physiological parameter, referred to as ground truth values, is determined. In the second step, the relevant sample PPG features can be selected based on the strength of correlation between the sample PPG feature and the ground truth values of the physiological parameter.

As part of selection of the relevant samples, the entire set of extracted sample PPG features can be divided in to one or more training sets and a testing set. In an example, the relevant samples can be extracted from the training set, whereas the testing set can be used for determining the relevance of the selected sample PPG features and the accuracy of the selection. in the training phase, the sample PPG features and the ground truth values of the physiological parameters are known, and on the basis of the sample PPG features and the ground truth values, values of the correlation coefficient for each sample PPG feature is determined. The value of the correlation coefficient of a sample PPG feature is then used to determine the gain factor for that sample PPG feature. In an example, a gain function curve can be used for determining the value of the gain factor. In said example, a slope of the gain function curve can be tuned for determining an optimal value of the gain factor for each sample PPG feature. The optimal gain factors so obtained are used in the testing phase. In the training phase, the Sample PPG features are multiplied by their optimal gain factors and then used for training classifier models for estimating the physiological parameter. On the other hand, during testing, the optimal gain factors can be multiplied by the respective Sample PPG features to estimate the physiological parameters.

Accordingly, in an implementation, a correlation coefficient for each of the plurality of Sample PPG features in the training set, based on the Sample PPG features and the ground truth values. The correlation coefficient can capture a relation between the Sample PPG feature and the ground truth value of the physiological parameter. In an example, the correlation coefficient can be a maximum information coefficient (MIC) value and can be determined based on the MIC techniques. Once the MIC values of the Sample PPG features are determined, strength of the correlation of between each Sample PPG feature and the ground truth values can be determined. Accordingly, a gain factor for each of the plurality of Sample PPG features can be determined, based on the correlation coefficient and a gain function. In an example, the gain function can be a sigmoid gain function.

As would be understood, the gain function, and therefore, the gain factor, can emphasize or highlight the Sample PPG features for which the strength of correlation is high, say based on a threshold value of the MIC value of the Sample PPG feature. Accordingly, in an implementation, each Sample PPG feature is multiplied with the respective gain factor for selecting the relevant samples. In an example, the Sample PPG features can be selected based on a threshold value of the gain factor. In another case, the Sample PPG features can be selected based on a threshold value of the Sample PPG feature. In both the above cases, when the Sample PPG feature is multiplied to the gain factor having a low value, say below the threshold value of the gain factor, the value of the Sample PPG feature is suppressed, i.e., falls below the threshold value of the Sample PPG feature, and such Sample PPG features can be discarded. Accordingly, the Sample PPG features for which the value is greater than the threshold value, or for which the value of the gain factor is greater than the threshold value, can be selected as the relevant samples.

Subsequently, the testing of the selected relevant features is carried out using the testing set, say previously selected from among the extracted Sample PPG features. In an implementation, the gain factor selected for each Sample PPG feature is employed with the Sample PPG features in the testing set for testing whether the Sample PPG features selected as relevant based on the gain factor are accurately selected or not. In an example, the Sample PPG features in the testing set can be multiplied with the respective gain factors determined for the training set. Based on the multiplication, it can be determined whether the same Sample PPG features are selected as the relevant samples from the testing set, as those selected from the training set.

Further, according to an implementation, the relevant samples selected above are deployed for estimating and monitoring the physiological parameter in real time. Accordingly, in an embodiment, based on the relevant sample PPG features and the ground truth values of the physiological parameter, a mathematical model is determined. The mathematical model captures the relationship between the relevant sample PPG features and the ground truth values of the physiological parameter. According to an aspect, the mathematical model can be determined based on the relevant sample PPG features and the ground truth values of the physiological parameter, using supervised learning techniques. The mathematical model, so determined, can be used for estimating the ground truth values for the physiological parameter based on a PPG waveform and Sample PPG features, and vice-versa.

In an implementation, before the mathematical model is deployed further, the mathematical model can be checked for accuracy. In an example, the mathematical model can be used, in a trial environment, for estimating a physiological parameter bin indicating a range of values within which the measured value of the physiological parameter lies. The estimated physiological parameter bin can be compared to an actual known value of the physiological parameter to determine whether the mathematical model is accurate or not. In case the mathematical model is not accurate, training of the mathematical model is achieved to enhance accuracy. For instance, further PPG waveforms for various sample subjects can be obtained, and processed in the same manner as described above, to refine the mathematical model.

In an embodiment, the mathematical model can be provided on the physiological parameter monitoring device, referred to as the device hereinafter, for monitoring the physiological parameter associated with a test subject. In an implementation, for monitoring the physiological parameter using the device having the mathematical model deployed therein, a video of the test subject can be captured using a camera of the device. In an implementation, the video can be subsequently processed by the device to obtain a test PPG waveform from which the test Sample PPG features are extracted. In one example, the test PPG waveform is obtained from the video in the same manner as described for obtaining the sample PPG waveform. In addition, the test Sample PPG features can be the same as the sample PPG features. In another case, the device can extract the Sample PPG features corresponding to the relevant sample PPG features.

In an implementation, to ascertain the physiological parameters, a plurality of determinant windows covering a predetermined number frames is chosen from among the determinant windows. In an example, the determinant windows covering, in total, last 512 frames of the consistent windows are selected for measuring the physiological parameters. Further, the present subject matter provides for performing an additional step to check whether the selected determinant windows are effective for determining the physiological parameters. Accordingly, in an implementation, a peak frequency detection check is performed for each of the selected determinant windows. In an example, in case the physiological parameter being measured is the heart rate, the peak frequency detection check is performed to check the frames for consistency of the peak frequency. In an example, the peak frequency detection check can be indicative of a periodicity of the pulse of the subject.

Once the above mentioned check is performed and the selected determinant windows pass the peak frequency detection check, the peak frequency of the quantized colour value for each selected determinant window is determined. In an example, the peak frequency for each selected determinant window can be determined by applying Fast Fourier Transform (FFT) to the quantized colour value of each frame in the selected windows. In another example, the peak frequency for each of the selected determinant window can be determined by applying STFT technique to the quantized colour values of the respective frames in the selected windows. Accordingly, the peak frequencies of the quantized colour value, considering all the frames in the selected determinant windows, are used to determine the physiological parameters associated with the subject. On the other hand, if one or more selected determinant windows fail the peak frequency detection check, then a prompt or a feedback can be provided to the subject for capturing a new video.

Further, in case the video is consistent, the device can estimate the physiological parameter and monitor the same, based on the test features and the mathematical model. In an example, the device, and the mathematical model deployed therein, can indicate the physiological parameter bin estimated for the physiological parameter. Therefore, in said example, the estimation done based on the mathematical model can be indicative in nature, instead of being quantitative measurement. In such a case, the estimation in accordance with the present subject matter provides for a methodology by way of which the physiological parameters and conditions of the subject can be monitored, for example, to keep a track of the medical condition of the subject so that appropriate medical aid can be provided to the subject in due time.

The present subject matter provides for an accurate determination of the physiological parameters at the same time involving less temporal and computational resources for measuring the physiological parameters. For example, the measurement of the physiological parameters is substantially devoid of inaccuracies because of movement of the subject, since the video is checked for consistency. In addition, when the video is determined to be inconsistent, the subject is notified and informed of the error. Accordingly, the subject can recapture the video for determining the physiological parameters. As a result, erroneous measurement of the physiological parameters, and the consequences thereof, are prevented. In addition, since the measurement can be done by a hand held device, which is convenient for using. For example, the present subject matter is convenient in measuring the physiological parameters for aged persons or those in an immovable condition.

Further, with the selection of few relevant sample PPG features from the entire set of Sample PPG features extracted from the video, the accuracy of estimation of the physiological parameter and the monitoring thereof is considerably high. In addition, since during the estimation of the physiological parameter a less number of features are to be analyzed and processed, the computational resources and time involved in monitoring the physiological parameter are substantially less. Therefore, such a model can even be deployed on devices having low processing capabilities. Consequently, the monitoring of the physiological parameters in accordance with the present subject matter is easily scalable and can be made highly available.

In addition, the inclusion of the physical characteristics of the sample subject further enhances the accuracy in estimation of the physiological parameters, since such factors affecting the physiological parameters are taken into account while estimating the physiological parameters. Further, the use of such physical characteristics in combination with the features extracted from the PPG waveform provides for accurate estimation of physiological parameters, such as blood pressure and ECG features, as inputs from other sensing devices are not required. Accordingly, in an aspect of the present subject matter, the physiological parameters can be estimated and monitored on the basis of only relevant sample PPG features. For example, the mathematical model can be determined based on only the relevant sample PPG features and the ground truth values of the physiological parameter to be monitored. As a result, the present subject matter provides for an accurate monitoring of the physiological parameters and, at the same time, the equipment used for such monitoring can be provided as being portable and easy to handle, say in a hand held device such as a mobile phone.

These and other advantages of the present subject matter would be described in greater detail in conjunction with the following figures. While aspects of described systems and methods for monitoring physiological parameters can be implemented in any number of different computing systems, environments, and/or configurations, the embodiments are described in the context of the following device(s).

FIG. 1 illustrates a modeling system 100 coupled for facilitating monitoring of physiological parameters associated with a subject, in accordance with an embodiment of the present subject matter. In an implementation, the modeling system 100, based on photoplethysmographic (PPG) techniques and known values of the physiological parameters, can determine a correlation between a PPG waveform and the physiological parameters. This correlation can then used for monitoring physiological parameters in real time. In an example, the modeling system 100 can be implemented as a workstation, a personal computer, say a desktop computer or a laptop, a multiprocessor system, a network computer, a minicomputer, or a server.

In one implementation, the modeling system 100 includes processor(s) 102 and memory 104. The processor 102 may be implemented as one or more microprocessors, microcomputers, microcontrollers, digital signal processors, central processing units, state machines, logic circuitries, and/or any devices that manipulate signals, based on operational instructions. Among other capabilities, the processor(s) is provided to fetch and execute computer-readable instructions stored in the memory 104. The memory 104 may be coupled to the processor 102 and can include any computer-readable medium known in the art including, for example, volatile memory, such as Static Random Access Memory (SRAM) and Dynamic Random Access Memory (DRAM), and/or non-volatile memory, such as Read Only Memory (ROM), erasable programmable ROM, flash memories, hard disks, optical disks, and magnetic tapes.

Further, the modeling system 100 may include module(s) 106 and data 108. The modules 106 and the data 108 may be coupled to the processors 102. The modules 106, amongst other things, include routines, programs, objects, components, data structures, etc., which perform particular tasks or implement particular abstract data types. In addition, the modules 106 may be implemented as signal processor(s), state machine(s), logic circuitries, and/or any other device or component that manipulate signals based on operational instructions.

In an implementation, the module(s) 106 include a processing module 110, a consistency analysis module 112, feature selection module 114, a testing module 116, a modeling module 118, and other module(s) 120. The other module(s) 120 may include programs or coded instructions that supplement applications or functions performed by the modeling system 100. Additionally, in said implementation, the data 108 includes a processing data 122, a consistency analysis data 124, a feature data 126, a modeling data 128, and other data 130. The other data 130 amongst other things, may serve as a repository for storing data that is processed, received, or generated, as a result of the execution of one or more modules in the module(s). Further, although the data 108 is shown internal to the modeling system 100, it may be understood that the data 108 can reside in an external repository (not shown in the figure), which may be operably coupled to the modeling system 100. Accordingly, the modeling system 100 may be provided with interface(s) (not shown) to communicate with the external repository to obtain information from the data 108.

In addition, for operation, the modeling system 100 can be coupled to a sampling device 132 to obtain the PPG waveform associated with a sample subject. Further, the modeling system 100 interfaces with a physiological parameter monitoring device 134 which uses the correlation and monitors the physiological parameters for a test subject, such as a patient. In an example, the physiological parameter monitoring device 134 can be a hand held device having a processor for providing processing capabilities. For instance, the physiological parameter monitoring device 134 can be a mobile phone, personal digital assistant (PDA), smart phone, or a tablet personal computer.

In operation, the sampling device 132 captures a video of the sample subject for whom ground truth values of a physiological parameter for which the correlation is to be modeled are known. As will be understood, the ground truth values are the actual known values of the physiological parameter. In an example in which the physiological parameter is blood pressure, the ground truth values can be values of systolic blood pressure and diastolic blood pressure. In another example in which the physiological parameter is the ECG features for monitoring heart condition, the ground truth values can be values of ECG features, say QRS complex, PR interval, RR interval, and QT interval.

In an example, for capturing the video, the subject can position a body part 136 in contact with a lens of a camera 138, or vice-versa, while a flash light of the camera 138 is switched on. For instance, the subject can position a finger tip of his hand on the camera 138 for capturing the video. In another example, the video can be captured from an ear lobe of the subject. In such position, the video of the body part 136 of the subject is captured using the camera 138 of the sampling device 132. In an example, the flash light can be a light-emitting diode (LED) type of flash light and can provide appropriate illumination to the body part 136 for effectively capturing the video for further processing. In one example, the camera 138 of the sampling device 132 can capture the video at a rate of about 30 frames per second (fps).

Further, the video can be processed and checked for consistency analysis, and subsequently, used for determining the physiological parameters. In one example, the sampling device 132 can provide the video to the modeling system 100 and the video can be processed by the processing module 110.

According to an implementation, the processing module 110 and the consistency analysis module 112 can be together implemented as a finite state machine (FSM) for determining the consistency of the video. Accordingly, the processing module 110 can be in an acquiring state in which the processing module 110 obtains a video from the sampling device 132 for further analysis. Once the video is obtained, the state of the FSM can change to an analysis state, during which the processing module 110 can process the video and the consistency analysis module 112 determines the consistency of the video.\

In an implementation, the processing module 110 processes and analyzes the video to obtain a plurality of windows and each window includes a predetermined number of frames. In an example, the processing module 110 processes the video to obtain such windows that certain frames of one window overlap certain frames of the adjacent windows. As would be understood, the term adjacent as used above is in context to the windows lying on a time axis. For instance, the processing module 110 obtains 12 consecutive windows each having 64 frames from the video, and each window of 64 frames is shifted by 48 frames which means that 16 frames of one window overlap 16 frames of consecutively succeeding window.

In an implementation, as part of processing of the video, the processing module 110 can determine one or more quantized colour value for each frame in the plurality of windows. In an example, the processing module 110 can determine the quantized colour value for a certain colour model. For instance, in which the colour model is the Red-Green-Blue (RGB) colour model, the processing module 110 can determine an average value of any one of the red, blue, or green component for each frame and that value can be the quantized colour value. In another case, in which the colour model is the Hue-Saturation-Value (HSV) model, the processing module 110 can determine the average value of any one of the hue, saturation, or value components of the colour model for each frame, and such average value can be the quantized colour value. The quantized colour values of the frames can be stored in the processing data 122.

In addition, the processing module 110 can check the captured video for effectiveness, for example, whether the video has sufficient clarity and illumination for determining the physiological parameters. According to said implementation, the processing module 110 can compare the quantized colour value for each frame to a predetermined range of quantized colour values to, say check whether the quantized colour value is within the predetermined range. For instance, from the comparison, the processing module 110 can determine a first occurrence of a blood signal in the frames, the blood signal being indicative of blood pulsating in blood vessels under the skin of the body part, say the finger tip. In an example, the processing module 110 can determine the quantized colour values of saturation components and hue components for 8 consecutive frames of the video for determining the blood signal.

In case the quantized colour value is within the predetermined range, then it indicates that the captured frames are ineffective for determining the physiological parameters. Accordingly, the processing module 110 can generate a feedback, say in the form of a pop-up message on a screen of the device 132, for the subject to reposition the camera 138 or the body part 136 with respect to the other, to capture a new video for analysis and for determining the physiological parameters. On the other hand, if the quantized colour value is beyond the predetermined range, then the consistency analysis module 112 can use the captured video further analysis. The predetermined range of quantized colour values can be stored in the processing data 122.

As mentioned previously, once the acquiring state is completed, the state changes to analysis state and the consistency analysis module 112 can determine the consistency of the video. According to an aspect, the consistency analysis module 112 can perform the consistency analysis for the video, on the basis of peak frequency of the quantized value of colours in the frames of the video. In an example, the consistency analysis module 112 can apply Short-Term Fourier Transform (STFT) technique to the quantized colour value of the frames to determine the peak frequencies, for consistency analysis. In the above examples, the consistency analysis module 112 can apply the STFT or FFT techniques to the quantized colour values to generate a sample PPG waveform.

Accordingly, the consistency analysis module 112 can obtain a few windows from the plurality of windows, referred to as determinant windows, and perform the consistency analysis for the determinant windows. In an example, in which 12 windows of 64 frames shifted by 48 are obtained from the video, the consistency analysis module 112 can analyze the consistency of the video once 11 such determinant windows are obtained for which the quantized colour values of frames is within the predetermined range. Therefore, in one example, such windows, from the plurality of windows, for which the quantized values of frames are within the predetermined range, can be used further for consistency analysis can be referred to as determinant windows. In said implementation, the consistency analysis module 112 can determine a position of peak frequency of the quantized colour value for each determinant window for consistency analysis.

In one example, the consistency analysis module 112 can determine the position of peak frequency in each determinant window based on the quantized value of colours in the frames of the respective determinant window. The positions of peak frequencies determined for the frames are stored in the consistency analysis data 124. Subsequently, for analyzing the video, the consistency analysis module 112 can assess a frequency drift for the peak frequencies across the determinant windows. In an example, the frequency drift is indicative of variation in position of peak frequency across the determinant windows. In one case, the frequency drift for the peak frequencies across the determinant windows can be determined by comparing the position of peak frequency in one window to the position of peak frequency in every other window, for all the determinant windows.

Further, the consistency analysis module 112 can compare the determined frequency drift against a threshold frequency drift, and in case the frequency drift is beyond the threshold, it indicates that the determinant windows and, therefore, the video, are inconsistent. On the other hand, in case the consistency analysis module 112 ascertains that the frequency drift is within the threshold frequency drift, the condition referred to as frequency lock, then according to an aspect of the present subject matter, the consistency analysis module 112 can perform another check to corroborate the consistency of the video. The threshold frequency drift is stored in the consistency analysis data 124.

Accordingly, in an implementation, the consistency analysis module 112 can determine a signal amplitude of the quantized colour value, for example, amplitude of the quantized colour value, for each frame in the determinant windows, and compares the signal amplitude against a threshold signal amplitude. In case the consistency analysis module 112 determines that the signal amplitude of all the frames is greater than the threshold signal amplitude, it is indicative of the consistency of the video captured for determining the physiological parameters. In case the captured video is determined to be inconsistent, the consistency analysis module 112 can provide a feedback to the subject for capturing a new video.

As will be understood from the foregoing description, as long as the consistency of the video is not established, the FSM, comprised of the processing module 110 and the consistency analysis module 112, continuously shuffles between the acquiring state and the analysis state. Once the consistency of the video is established, FSM changes the state to the model state. In the model state, the feature selection module 114, the testing module 116, and the modeling module 118 can model the mathematical model from the processed consistent video.

Further, the processing module 110 can analyze the sample PPG waveform and obtain a plurality of sample PPG features from the sample PPG waveform. In an example, the sample PPG features extracted from the sample PPG waveform can include a set of time domain features or a set of frequency domain features, or both. For instance, the set of time domain features can include a peak-to-peak time interval for the peaking frequencies in the sample PPG waveform, pulse interval, crest time indicative of the time taken for the sample PPG waveform to reach the peaking frequencies, diastolic time, height of the pulse, and area under the sample PPG waveform.

The determination of the sample PPG features from the PPG waveform by the processing module 110 can be understood with the help of the following illustrations. Consider a case in which the sample PPG features are obtained for determining a model for estimating blood pressure of a subject. In such a case, for obtaining the Sample PPG features, from the sample PPG waveform a systolic peak $(T_{sn}, A_{sn})$, a valley point $(T_{vn}, A_{vn})$, and a dicrotic notch $(T_{dn}, A_{dn})$ are determined, say in the time domain. In said example, T denotes time instant and A denotes the amplitude for the above mentioned features of the sample PPG waveform. For instance, the processing module 110 can determine the systolic peak and the valley point based on local maxima and minima points from the PPG waveform, say a function representative of the PPG waveform. Further, in said example, the processing module 110 can determine the dicrotic notch by first determining a derivative of the function representing the PPG waveform and then identifying a first local maxima between the systolic peak of one PPG waveform and the valley point of the adjacent PPG waveform peak.

Based on the aforementioned parameters associated with the PPG waveform, various sample PPG features are determined. Such sample PPG features can include, for example, a valley amplitude ($A_{vn}$) measured at the valley point, a systolic peak amplitude ($A_{sn}$) measured at the systolic peak, a dicrotic notch amplitude ($A_{dn}$) measured at the dicrotic notch, and a systolic area which is indicative of an area under the PPG waveform between the systolic peak and the dicrotic notch, and a dicrotic notch area which is an area under the PPG waveform between the dicrotic notch of one PPG waveform peak and a valley point of the subsequent PPG waveform peak. In an example, the systolic area and the dicrotic area can be determined using the following respective equations:

Systolic area=$\Sigma_{Tsn}^{Tdn} P$,

Dicrotic area=$\Sigma_{Tdn}^{Tvn+1} P$, where $P$ denotes the equation for the PPG waveform.

In addition, in said example, the sample PPG features obtained based on the aforementioned parameters can include a total area under the PPG waveform, say measured as a summation of the systolic area and the dicrotic area, and a ratio of area, say measured as ratio of dicrotic area to the systolic area. Further, the sample PPG features can include, for example, a peak interval determined as time interval between systolic peaks of two adjacent PPG waveform peaks, a pulse height determined as an amplitude of the systolic peak measured from the valley of the PPG waveform, and a pulse interval measured as time between the valley points of adjacent PPG waveform peaks. In one example, the total area, the ration of area, the peak interval, the pulse height, and the pulse interval are determined based on the following respective equations:

Total area=Systolic area+Dicrotic area

Ratio of area=Dicrotic area/Systolic area

Peak interval=$T_{sn+1}-T_{sn}$.

Pulse height=$A_{sn}-A_{vn}$

Pulse interval=$T_{vn+1}-T_{vn}$

Furthermore, in an example, the sample PPG features can include a crest time determined as the time difference between the systolic peak and the valley point of the same PPG waveform peak, a delta time indicative of a time difference between the dicrotic notch and the systolic peak of the same PPG waveform peak. In addition, the sample PPG features can include an augmentation index and a reflection index. The crest time, the delta time, the augmentation index, and the reflection index can be determined using the following equations as an example:

Crest time=$T_{sn}-T_{vn}$

Delta time=$T_{dn}-T_{sn}$

Augmentation index=$(A_{dn}-A_{vn})/(A_{sn}-A_{vn})$

Reflection index=1−augmentation index

Consider another case in which the sample PPG features are obtained for determining a model for estimating ECG features of the subject. In an example, in such a case also, for obtaining the Sample PPG features, from the sample PPG waveform a systolic peak ($T_{sn}$, $A_{sn}$), a valley point ($T_{vn}$, $A_{vn}$), and a dicrotic notch ($T_{dn}$, $A_{dn}$) are determined from the sample PPG waveform, where T denotes time instant and A denotes the amplitude for the above mentioned features of the sample PPG waveform. Based on coordinates of the systolic peak, the valley point, and the dicrotic notch, various sample PPG features associated with the PPG waveform are obtained.

In an example, in such a case of ECG feature estimation, the sample PPG features can include a peak to peak interval which is determined as time interval between systolic peaks of two adjacent PPG waveform peaks, the pulse interval measured as time between the valley points of adjacent PPG waveform peaks, the pulse height determined as an amplitude of the systolic peak measured from the valley of the PPG waveform, the crest time indicative of the time difference between the systolic peak and the valley point of the same PPG waveform peak, the delta time measured as the time difference between the dicrotic notch and the systolic peak of the same PPG waveform peak. In one example, such sample PPG features are determined using the same respective equations as mentioned above.

In addition, in case of ECG features estimation, the sample PPG features can include a dicrotic time which is determined as a time interval between the valley point and the dicrotic notch of the same PPG waveform peak, a falling time indicative of a time interval between the systolic peak of one PPG waveform peak and the valley point of the adjacent PPG waveform peak, a dicrotic to minima time indicative of the time interval between the dicrotic notch of one PPG waveform peak and the valley point of the adjacent PPG waveform peak, a rising slope of the PPG waveform measured for the rising portion of the PPG waveform from the valley point to the systolic peak, and a falling slope of the PPG waveform measured for the falling portion of the PPG waveform from the systolic peak to the valley point of the adjacent PPG waveform peak. In an example, the dicrotic time, the falling time, the dicrotic to minima time, the rising slope, and the falling slope are determined based on the following equations, respectively:

Dicrotic time=$T_{dn}-T_{vn}$

Falling time=$T_{vn+1}-T_{sn}$

Dicrotic to minima time=$T_{vn+1}-T_{dn}$

Rising slope=$(A_{sn}-A_{vn})/(T_{sn}-T_{vn})$

Falling slope=$(A_{vn+1}-A_{sn})/(T_{vn+1}-T_{sn})$

Further, according to an aspect, physical characteristics associated with the sample subject can also be taken into account as the sample PPG features. For instance, the physical characteristics can include weight of the subject, height of the subject, and age of the sample subject. In said example, as would be understood from the foregoing description, the processing module 110 can obtain the sample PPG features in time domain or in the frequency domain or both. For instance, the processing module 110 can extract the Sample PPG features in the frequency domain, say from the amplitude-frequency curve. In an example, the processing module 110 can extract location of dominant peak frequency, distance between the dominant peak frequency and the immediate peak frequency, spectral centroid, and width of dominant peak frequency region, as the frequency domain features. In an example, for obtaining the frequency domain features, the processing module 110 can segment the frames in the sample video into non-overlapping rectangular windows of 1024 or 256 samples, to obtain sample PPG waveform in the manner as described above. Further, the processing module 110 can store the extracted sample PPG features, the extracted sample PPG features forming the set of sample PPG features obtained or extracted from the sample video, in the processing data 122.

Further, in an implementation, the feature selection module 114 can select one or more relevant sample PPG features from the set of sample PPG features. In an implementation, before the relevant sample PPG features are selected from the set of sample PPG features, the processing module 110 can remove intermediate false peaks or trough points from the Sample PPG features to remove noise from the Sample PPG features. Otherwise, actual peaks or trough points may be completely missed out due to noisy surroundings and may result in the incorrect calculation of Sample PPG features during extraction of the Sample PPG features. In an example, the processing module 110 can create two clusters of the Sample PPG features. Further, based on a histogram analysis, the processing module 110 can initialize the centroids for the cluster analysis. Subsequently, the processing module 110 can apply a 2-Means clustering followed by cluster density estimation to remove the incorrect Sample PPG features. In another case, the processing module 110 can apply k-means algorithm to obtain the cluster centroids. Further, the processing module 110 can employ Xie-Beni index for removing the incorrect Sample PPG features and obtaining the set of Sample PPG features which can be used for selection of the relevant samples.

Further, in accordance with an aspect of the present subject matter, the feature selection module 114 can select one or more relevant sample PPG features from the plurality of sample PPG features.

In accordance with an aspect of the present subject matter, the feature selection module 114 can follow a two-step approach for selecting the relevant PPG features from the entire set of extracted PPG features. In the first step, the feature selection module 114 can determine the correlation between the PPG features and the ground truth values of the physiological parameter. Further, in the second step, the features selection module 114 can select the relevant PPG features based on the strength of correlation between the PPG feature and ground truth values of the physiological parameter.

According to an implementation, as part of selection of the relevant PPG features, the feature selection module 114 can divide the entire set of extracted PPG features into one or more training sets and a testing set and store the same in the feature data 126. In an example, the feature selection module 114 can extract the relevant PPG features from the training set, and use the testing set to determine accuracy of the selection of the relevant PPG features.

Accordingly, the feature selection module 114 can determine a correlation coefficient for each of the plurality of PPG features in the training set, based on the PPG features and the ground truth values. The correlation coefficient can capture a relation between the PPG feature and the ground truth value of the physiological parameter. In an example, the feature selection module 114 can determine a maximum information coefficient (MIC) value as the correlation coefficient, based on the MIC techniques. In an example, the feature selection module 114 can construct grids with various sizes to find the largest mutual information between the data pair, i.e., between the PPG feature and the ground truth value. For each pair of data (x, y), if I is the mutual information for a grid G, then MIC of a set D of pair-wise data with sample size n and grid size (xy), the feature selection module 114 can determine the correlation coefficient, i.e., the MIC value based on the following relation as an example:

$$\mathrm{MIC}(D) = \max_{xy < B(n)} \{M(D)_{x,y}\} \quad (1)$$

In the above mentioned relation (1), the expression $\{M(D) x, y\}$ measures a normalized mutual information between the data pair (x, y). In addition, in relation (1), the grid size (xy) is less than B(n), where B(n) is a function of the sample size and can be, for example, provided by the following relation:

$$B(n) = n^{0.6}$$

Further, for different distributions of the grid G, M(D) can be provided by the following expression as an example:

$$M(D)_{x,y} = \frac{\max\{I(D \mid G)\}}{\log\min(x, y)}$$

Once the MIC values of the PPG features are determined, the feature selection module 114 can determine the strength of the correlation of between each PPG feature and the ground truth values. Accordingly, according to an aspect, the feature selection module 114 can determine a gain factor for each of the plurality of PPG features, based on the correlation coefficient and a gain function.

In an example, the gain function can be a sigmoid gain function and can translate the values of the PPG features ranging from $-\infty$ to $\infty$ to between 0 and 1. In said example, the feature selection module 114 can determine the gain factor ($G_n$) based on the following sigmoid function as an example:

$$G_n = \frac{1}{1 + e^{-m \cdot (w_n - 0.5)}}$$

In the above expression, $w_n$ can be the correlation coefficient, say the MIC value, of a PPG feature associated with the ECG and 0.5 can be a threshold value of the coefficient correlation. While, in the above case, the threshold value is selected to be the midway of the maximum MIC value, i.e., 1, in other examples, the threshold values can be selected to be other than 0.5. In said example, the gain factor can assign a weightage to each of the PPG features with respect to the ground truth based on the MIC values obtained. For instance, if the MIC value is obtained high, i.e., greater than about 0.5, then according to the equation for $G_n$, the gain factor becomes close to 1 and if the obtained MIC value is low, that is less than about 0.5, the gain factor for that PPG features is close to zero. Further, the constant m controls a slope or steepness of a curve of the gain function, i.e., when the gain factor is plotted against the correlation coefficient. In effect, as is evident from the above relation, the value of m can determine the value of the gain factor. For example, the function forms a horizontal line at m=0, resulting in a gain factor of 0.5 for all values of the correlation coefficient. This can be understood to be equivalent to a no feature selection criteria.

Accordingly, in an implementation, the feature selection module 114 can multiply each PPG feature with the respective gain factor for selecting the relevant PPG features. Considering the above example of the relation, the gain factor is dictated by the selection of the slope constant m of the gain function curve. In said implementation, the feature selection module 114 can increase the value by predetermined increments in order to determine an optimal value of m, and therefore, an optimal value of the gain function for each of the PPG features. Such incrementing of the slope constant m in predetermined steps is referred to as tuning of the slope constant m.

According to an implementation, to determine the optimal value of the gain function, the feature selection module 114 can employ a k-fold validation technique. According to said technique, in an example, the feature selection module 114 can use the training data set to determine the PPG features by tuning the value of the slope constant m, i.e., based on different values of the slope constant m, using a classifier model. In an example, the classifier model can be is one of a support vector machine (SVM)-based model and an adaptive neural network (ANN)-based model. In said example, based on the accuracy of the PPG features determined, the value of the gain function can be determined. In said example, the determined PPG features can be compared with a known ground truth values to determine the accuracy of determining the PPG features. Further, the gain factor for the accurately determined PPG features can be selected as the optimal gain factor.

In another example, based on the accurately determined PPG features, the optimal value of the slope constant m can be determined. In such a case, based on the optimal value of the slope constant m, the value of the gain factor can be determined from the equation for gain factor Gn. Further, in another implementation, the feature selection module 114 can use a regression model as a predictor model instead of a classifier model, for predicting the values of the physiological parameters to determine the values of PPG features by tuning the values of the slope constant m. In one case, the regression model can be one of a linear regression model, a non-linear regression model, and a polynomial regression model.

Further, once the gain factor is determined, the feature selection module 114 can select the PPG features selected based on a threshold value of the gain factor. In another case, the feature selection module 114 can select the PPG features based on a threshold value of the PPG feature. For example, when the feature selection module 114 multiplies the PPG feature to the gain factor having a low value, say below the threshold value of the gain factor, the value of the PPG feature is suppressed, i.e., falls below the threshold value of the PPG feature, and such PPG features can be discarded. Accordingly, the feature selection module 114 can select those PPG features as the relevant PPG features for which the value is greater than the threshold value, or for which the value of the gain factor is greater than the threshold value. In an example, while the strength of the correlation between the PPG features and the ground truth values is given by the correlation coefficient, the gain factor amplifies the strength value and provides a convenient and accurate manner of selecting the relevant PPG features based on the strength of the correlation.

While in the above description, the selection of the relevant sample PPG features by the feature selection module 114 is described based on maximal information coefficient (MIC) concept, the feature selection module 114 may select the relevant sample PPG features using other techniques also. For example, the feature selection module 114 can employ Pearson product-moment correlation coefficient (PPMCC) concept for selecting the relevant sample PPG features. In another case, the feature selection module 114 can determine any linear or non-linear relationship between the sample PPG features and the ground truth values, and accordingly select the relevant samples. In addition, in an example, the feature selection module 114 can employ statistical analysis tools for relevant sample selection. For instance, the statistical analysis tools can use maximum asymmetry score (MAS) technique, maximum edge value (MEV) technique, and minimum cell value (MCV) technique.

Subsequently, the testing module 116 can achieve the testing of the selected relevant features using the testing set, say previously selected from among the extracted PPG features. In an implementation, the testing module 116 can use the gain factor selected for each PPG feature by the feature selection module 114 with the PPG features in the testing set for testing whether the PPG features selected as being relevant are accurately selected or not. In an example, the testing module 116 can multiply the PPG features in the testing set with the respective gain factors determined for the PPG features in the training set. Based on the multiplication, the testing module 116 can determine whether the same PPG features are selected as the relevant PPG features from the testing set, as those selected from the training set.

After the relevant sample PPG features have been selected, in an embodiment, the modeling module 118 can determine a mathematical model based on the relevant sample PPG features and the ground truth values of the physiological parameter. As will be understood, the mathematical model so determined captures the relationship between the relevant sample PPG features and the physiological parameter. According to an aspect, the mathematical model can be determined based on the relevant sample PPG features and the ground truth values of the physiological parameter, using supervised learning techniques. In the present case, since no direct relation exists between the ground truth values and the PPG features, supervised learning techniques are employed for modeling the relationship between the two. In one example, the modeling module 118 can use regression-based learning techniques, support vector machine (SVM)-based learning techniques, artificial neural network (ANN)-based learning techniques, or any other such learning technique for determining the mathematical model.

Further, as mentioned previously, in an example in which the physiological parameter is blood pressure, the ground truth values can be values of systolic blood pressure and diastolic blood pressure. In another example in which the physiological parameter includes ECG features for monitoring heart condition, the ground truth values can be values of the ECG features, such as QRS complex, PR interval, RR interval, and QT interval. The modeling module 118 can store the mathematical model in the modeling data 128. According to another implementation, instead of using the exact ground truth values for feature selection, the modeling module 118 can break the entire set of ground truth values into ranges or bins and determine the mathematical model based on the bins.

Further, the mathematical model can be used for estimating the ground truth values for the physiological parameter based on a PPG waveform and PPG features.

Although the above description is provided with the sample PPG waveform being obtained for one sample subject, in another implementation, the modeling system 100 can obtain the sample PPG waveforms for a plurality of sample subjects, and use the different sample PPG waveforms in the same manner as described above, to determine the mathematical model. In such a case, since the mathematical model is determined based on the ground truth values and PPG waveforms associated with different sample subjects, the adaptability of the mathematical model is high and can be used for accurately estimating and monitoring the physiological parameter.

In an implementation, before the mathematical model is deployed further for estimating and monitoring physiological parameters, the modeling module 118 can ascertain an accuracy of the mathematical model. In an example, the check of accuracy of the mathematical model can be conducted in a trial environment, for example, the modeling system 100 which is deployed in a development environment. In one case, the modeling module 118 can provide a set of PPG features obtained from the PPG waveform for a subject for whom the ground truth values of the physiological parameter are known, to the mathematical model. The mathematical model can, in turn, estimate a physiological parameter bin, i.e., a range of values within which the measured value of the physiological parameter lies. The modeling module 118 can further compare the estimated physiological parameter bin to the actual known value of the physiological parameter to determine whether the mathematical model is accurate or not. In case the mathematical model is not accurate, the modeling system 100 obtains further PPG waveforms for various sample subjects to train the mathematical model to enhance accuracy of the mathematical model.

Further, for deployment, the mathematical model is provided at the physiological parameter monitoring device 134, hereinafter referred to as the device 134, for monitoring the physiological parameter associated with a test subject. In other examples, the mathematical model can be provided as an application, say a downloadable application, which can be installed on a hand held device, such as the device 134. Further, as mentioned previously, in an example in which the physiological parameter is blood pressure, the ground truth values can be values of systolic blood pressure and diastolic blood pressure. In another example in which the physiological parameter includes ECG features for monitoring heart condition, the ground truth values can be values of the ECG features, such as QRS complex, PR interval, RR interval, and QT interval. Further, in an example, the device 134 can store the mathematical model in a modeling data 144 of the device 134.

In an implementation, for monitoring the physiological parameter using the device 134 having the mathematical model deployed therein, a video of a body part 140, such as a finger or an ear lobe, of the test subject can be captured using a camera 142 of the device 134. Further, a monitoring module 146 of the device 134 can process the video to obtain a test PPG waveform in the same manner as described above with reference to the sampling device 132, say based on the quantized colour values and peak frequencies thereof. For instance, the monitoring module 146 can obtain, from among the determinant windows for which the frequency lock condition is determined to be true, a plurality of determinant windows having, in total, a predetermined number of frames. In an example, the monitoring module 146 selects those determinant windows which cover the last 512 frames of the consistent determinant windows, for measuring the physiological parameters. Selecting such frames from the consistent windows ensures that any errors due to stabilization of the flash light of the camera 138, which may adversely affect accuracy of measurement of the physiological parameters, are prevented.

Further, the monitoring module 146 can provide for performing an additional step to check whether the selected determinant windows are effective for determining the physiological parameters. Accordingly, in an implementation, the monitoring module 146 can perform a peak frequency detection check for each of the plurality of selected determinant windows. In an example, in case the physiological parameter being measured is the heart rate, the monitoring module 146 can perform the peak frequency detection check for determining the consistency of the peak frequency in the selected determinant windows.

In an example, the peak frequency detection check can be indicative of a periodicity of the pulse of the subject. The periodicity of the pulse, in turn, can be indicative of a video which can be effectively used for physiological parameters measurement. In case the one or more of the frames fail the peak frequency detection check, then the monitoring module 146 can provide a feedback to the subject for capturing a new video for analysis. In another implementation, the monitoring module 146 can select another set of determinant windows covering the predetermined number of frames, in the event of the frames failing the peak frequency detection check.

Subsequent to performing the peak frequency detection check, the monitoring module 146 can extract the test PPG features from the test PPG waveform. In an example, the test PPG features can be the same as the sample PPG features. In another case, the monitoring module 146 can extract the PPG features corresponding to the relevant sample PPG features determined earlier by the processing module 110. In such a case, for instance, the modeling system 100 can provide the relevant sample PPG features stored in a feature selection data 148 to the sampling device 132, and the monitoring module 146 can obtain those PPG features from the test PPG waveform. Further, based on the test features and the mathematical model, the monitoring module 146 can estimate the physiological parameter and monitor the same.

In an example, for monitoring the physiological parameter, the monitoring module 146 can estimate the physiological parameter bin indicating a range of values within which the physiological parameter may lie. Therefore, in said example, the estimation and monitoring of the physiological parameter by the monitoring module 146 can be indicative in nature, instead of being quantitative measurement. In such a case, the monitoring module 146 can provide a mode of monitoring a medical condition of the subject, say over a prescribed period of time, based on the range of value in which the physiological parameter lies. Accordingly, in one example, the medical condition of the subject can be tracked so that appropriate medical aid can be provided to the subject in due time.

In one example, in which the monitoring module 146 monitors the BP values for the test subject, the physiological parameter bins can be "very low", "low", "normal", "high", and "very high". In said example, the monitoring module 146 monitors the BP level of the test subject to fall within the "very low" bin when the diastolic pressure is less than about 50 millimeters of mercury (mmHg) or the systolic pressure is less than about 70 mmHg. Further, the BP of the test subject falls in the "low" bin when the diastolic pressure lies approximately in the range of about 50 to 65 mmHg or the systolic pressure lies approximately within the range of about 70 to 100 mmHg, and in the "normal" bin when the diastolic pressure lies approximately in the range of about 65 to 90 mmHg or the systolic pressure lies approximately within the range of about 100 to 135 mmHg. In addition, the BP level of the test subject can be considered to fall within the "high" bin when the diastolic pressure lies approximately in the range of about 90 to 100 mmHg or the systolic pressure lies approximately within the range of about 135 to 160 mmHg, and within the "very high" bin when the diastolic pressure is greater than about 100 mmHg or the systolic pressure is above about 160 mmHg.

Considering another case in which the monitoring module 146 estimates the ECG features as part of monitoring the physiological parameters. In such a case, the physiological parameter bins can again be termed as "very low", "low", "normal", "high", and "very high". In one example, the monitoring module 146 can determine the ECG features associated with the test subject to be "very low" when the RR interval is less than about 0.6 milliseconds (ms), and the ECG features can be "low" when the PR interval is less than about 120 ms, the QRS interval is less than about 60 ms, the QT interval is less than about 350 ms, or the RR interval is approximately within a range of about 0.6 to 0.8 m. Further, in said example, the ECG features for the test subject can fall within the "normal" bin when the PR interval is approximately within a range of about 120 to 200 ms, the QRS interval is approximately within the range of about 60 to 100 ms, the QT interval is approximately within the range of about 350-470 ms, or the RR interval is approximately within the range of about 0.8 to 1 second (s). In addition, the ECG features for the test subject are determined to fall within the "high" bin when the PR interval is greater than about 200 ms, the QRS interval is greater than about 100 ms, the QT interval is greater than about 470 ms, or the RR interval is approximately within the range of about 1 to 1.2 s, and within the "very high" bin when the RR interval is greater than about 1.2 s.

Further, while the estimation of the physiological parameters is described with reference to the physiological parameter monitoring device 134, the monitoring of the physiological parameters can also be achieved in real-time at the modeling system 100. In such a case, the modeling system 100 having the mathematical model stored thereon, receives the PPG features extracted from the test video, and can estimate and monitor the physiological parameters in real time.

FIG. 2, FIG. 3, FIG. 4, FIG. 5, and FIG. 6 illustrate methods for monitoring physiological parameters of a subject using a hand held device, according to an implementation of the present subject matter. In one example, the methods are carried out by the modeling system 100 and the physiological parameters monitoring device 134, such as the hand held device, used for determining the physiological parameters. The methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network. In a distributed computing environment, computer executable instructions may be located in both local and remote computer storage media, including memory storage devices.

The order in which the methods are described is not intended to be construed as a limitation, and any number of the described method blocks can be combined in any order to implement the methods, or alternative methods. Additionally, individual blocks may be deleted from the methods without departing from the spirit and scope of the subject matter described herein. Furthermore, the methods can be implemented in any suitable hardware, software, firmware, or combination thereof.

With reference to the description of FIG. 2, FIG. 3, FIG. 4, FIG. 5, and FIG. 6 for the sake of brevity, the details of the components of the modeling system 100 and the physiological parameters monitoring device 134 for determining the physiological parameters associated with the subject, are not discussed here. Such details can be understood as provided in the description provided with reference to FIG. 1.

Figure 2:
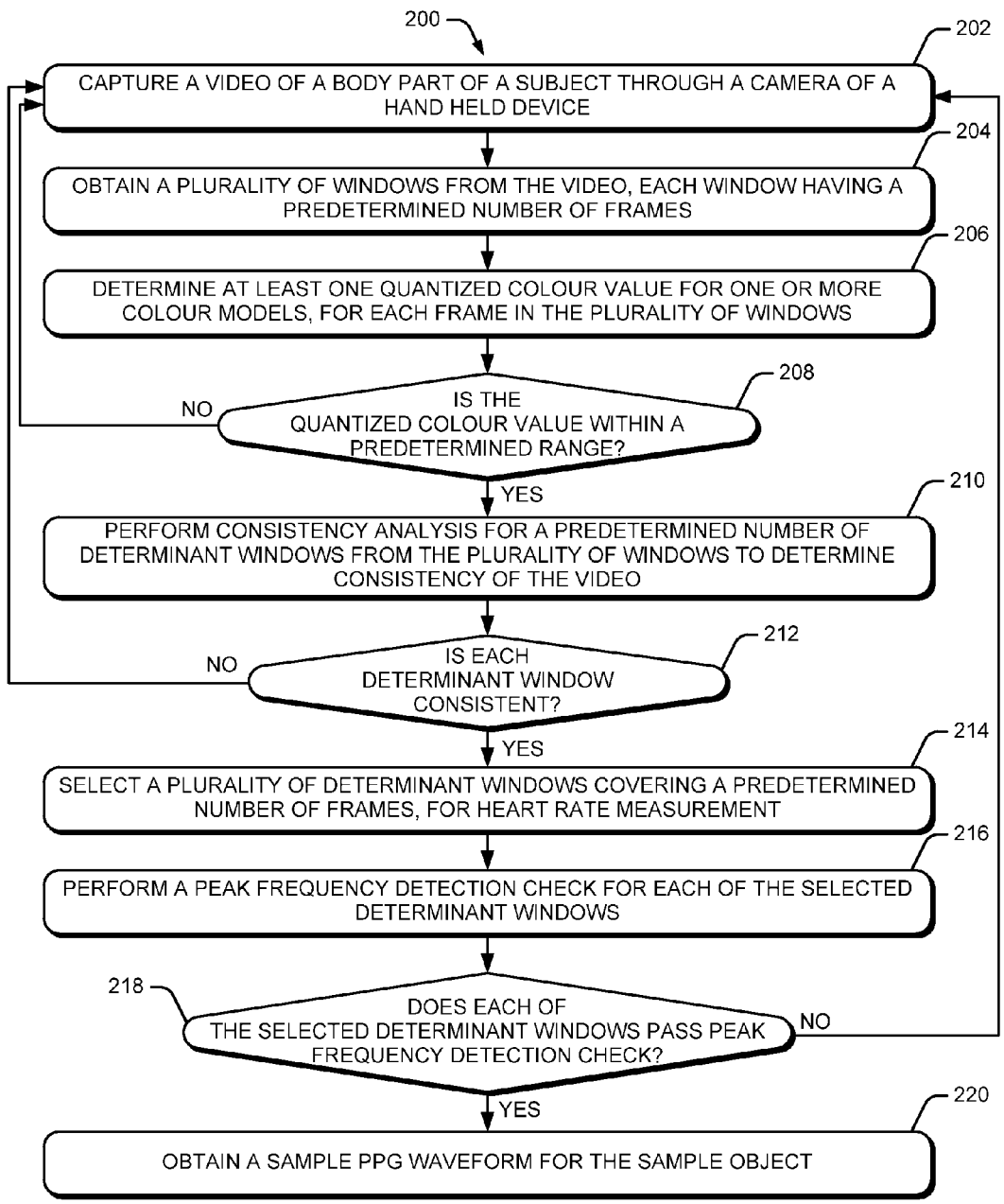
FIG. 2 illustrates a method 200 for performing consistency analysis of a video captured for monitoring the physiological parameters, in accordance with an implementation of the present subject matter.

FIG. 2 illustrates a method 200 for performing consistency analysis of a video captured for monitoring the physiological parameters, in accordance with an implementation of the present subject matter. Referring to FIG. 2, at block 202, a video of a body part 136 of the sample subject is captured using a camera 138 of a sampling device 132, which can be a hand held device. In an example, the video of a finger tip can be captured by positioning the finger tip against a lens of the camera 138 and having the flash light of the camera 138 switched on. Further, in case the camera 138 captures the video at a rate of 30 frames per second, the video can be captured for about 2 seconds.

At block 204, a plurality of windows, each having a predetermined number of frames, is obtained from the captured video. In an example, 12 windows each having 64 frames can be obtained from the video. For instance, the number of frames in each window can be based on the rate of video recording of the camera 138. Further, in one case, the windows from the video can be so obtained that certain frames of one window overlap certain frames of the adjacent windows. For instance, each window can have 64 frames with 16 frames overlapping with 16 frames of the consecutively succeeding or preceding window. As will be understood, the term adjacent is used in context of the time domain.

At block 206, at least one quantized colour value for each frame in the plurality of windows can be determined for a colour model. Accordingly, for instance, in which the colour model is the Red-Green-Blue (RGB) colour model, the quantized colour value can be an average value of any one of the red, blue, or green component, or a combination thereof. In another example, in case the colour model is the Hue-Saturation-Value (HSV) model, the quantized colour value can be an average value of any one of the hue, saturation, or value components of the colour model, or a combination thereof.

At block 208, it is determined whether the quantized colour value for each frame is greater than a predetermined range of quantized colour values. If the quantized colour value for one or more frames is within the predetermined range of values ('No' branch from block 208), then it indicates that the captured frames are ineffective for determining the physiological parameters. Accordingly, a feedback, say in the form of a pop-up message on the screen of the sampling device 132, can be provided to the sample subject to reposition the body part 136 with reference to the camera 138, or vice-versa, and a new video can be captured as described in block 202.

However, in case the quantized colour value for each frame is beyond the predetermined range of values ('Yes' branch from block 208), then at block 210 a consistency analysis is performed for a selected set of windows from the plurality of windows, to determine the consistency of the video. In an example, the windows from the plurality of windows for which the quantized values of frames are within the predetermined range are obtained for consistency analysis and are referred to as determinant windows. The consistency analysis of such windows is explained in detail with reference to FIG. 3.

At block 212, it is determined whether each of the determinant window is consistent, i.e., whether the video is consistent. If, block 212, it is determined that the video is inconsistent ('No' branch from block 212), then a notification can be provided as feedback to the sample subject to capture another video, as described at block 202.

Further, in case the video is determined to be consistent ('Yes' branch from block 212), then the physiological parameters of the subject can be determined. Accordingly, at block 214, a plurality of determinant windows covering a predetermined number of selected frames is chosen from among the determinant windows. Such determinant windows selected for determining the physiological parameters are referred to as selected determinant windows.

In addition, at block 216, a peak frequency detection check is performed for each of the selected determinant windows. In an example, in case the physiological parameter being measured is the heart rate, the peak frequency detection check is performed to check the selected determinant windows for consistency of the peak frequency. The peak frequency detection check can be performed at block 216 to determine whether the selected determinant windows of the video can be used for determining the physiological parameters or not. In an example, the peak frequency detection check can be indicative of a periodicity of the pulse of the sample subject.

Accordingly, at block 218, it is determined whether each of the selected determinant windows passes the peak frequency detection check or not. If one or more of the selected determinant windows fail the peak frequency detection check ('No' branch from block 218), then a notification or a pop-up message can be provided on the hand held device for the sample subject to capture another video as described with respect to the block 202. In another implementation, another set of determinant windows covering the predetermined number of frames can be selected at block 214 to determine the physiological parameters.

On the other hand, in case the selected determinant windows pass the peak frequency detection check ('Yes' branch from block 218), then at block 220 a sample PPG waveform is obtained for the sample subject. In an implementation, the sample PPG waveform for each selected determinant window can be ascertained by applying Fast Fourier Transform (FFT) to the quantized colour values of the frames covered by the selected determinant windows. In another implementation, the sample PPG waveform for each selected determinant window can be ascertained by applying Short-term Fourier Transform (STFT) to the quantized colour values of the frames covered by the selected determinant windows.

Figure 3:
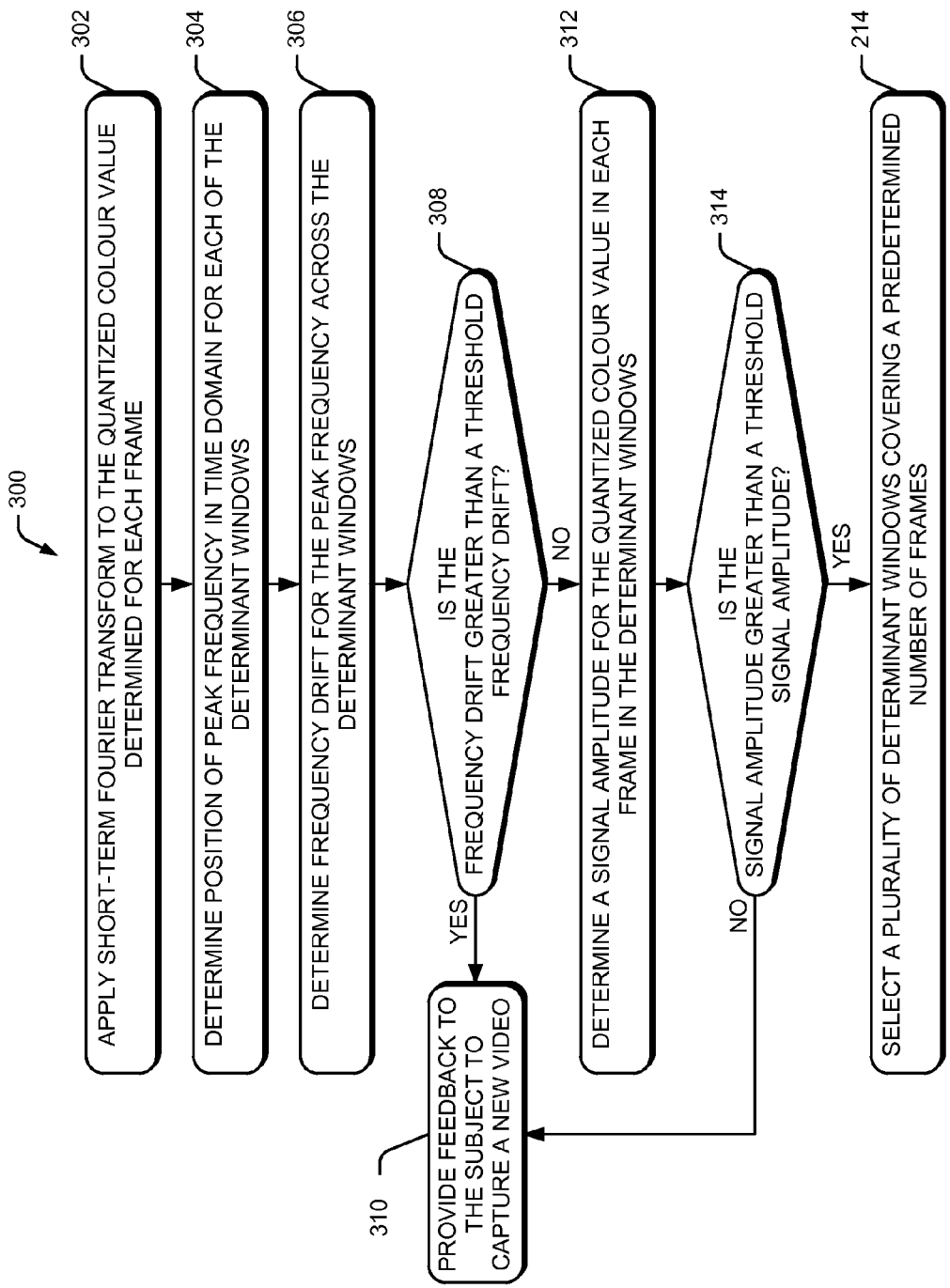
FIG. 3 illustrates the method 300 for analyzing consistency of a video capture using the hand held device, for determining the physiological parameters, in accordance with an implementation of the present subject matter.

FIG. 3 illustrates the method 300 for analyzing consistency of a video capture using the hand held device, for determining the physiological parameters, in accordance with an implementation of the present subject matter. As will be understood, the method 300 explains block 210 of FIG. 2 in detail.

As mentioned previously, the consistency analysis is performed on the basis of the sample PPG waveform, for example, peak frequencies of the quantized value of colours in the sample PPG waveform, obtained from the video.

Accordingly, at block 302, a Short-Term Fourier Transform (STFT) can be applied to the quantized colour value of each frame of the determinant windows, say to determine the sample PPG waveform and the peak frequencies in the sample PPG waveform, for consistency analysis. In an example, the consistency analysis commences when a predetermined number of determinant windows have been obtained.

At block 304, a position of peak frequency in time domain is determined for each determinant window, based on the peak frequencies determined at block 302 for each frame in the respective window.

Further, at block 306, a frequency drift for the peak frequencies across the determinant windows is determined. The frequency drift for the peak frequencies across the determinant windows can indicate that whether the position of the peak frequency in each window is stable or not. In an example, the frequency drift across the determinant windows can be determined by comparing the position of peak frequency in one window to the position of peak frequency in every other window, for all the determinant windows.

Subsequently, the determinant windows are analyzed based on the frequency drift to determine consistency of the video. Accordingly, at block 308 the determined frequency drift is compared against a threshold frequency drift to determine whether the frequency drift across the determinant windows is greater than the threshold frequency drift or not. In an example, as mentioned above, the comparison of the threshold frequency drift can be done with respect to the frequency drift determined for each pair of determinant windows.

In case the frequency drift is greater than the threshold ('Yes' branch from block 308), it indicates that the determinant windows and, therefore, the video, are inconsistent. Accordingly, at block 310, a feedback can be provided to the sample subject to capture a new video for determining the physiological parameters. In case, it is determined that the frequency drift is less than the threshold frequency drift ("No' branch from block 308), then another check can be performed for determining the consistency of the video.

For the other check, at block 312, a signal amplitude of the quantized colour value, for example, amplitude of the quantized colour value, for each frame in the determinant windows is determined. Further, at block 314, the signal amplitude for each frame of the determinant windows is compared against a threshold signal amplitude. In case the signal amplitude for one or more frames of the determinant windows is less than the threshold signal amplitude ('No' branch from block 314), it indicates that the video is inconsistent and, subsequently, at block 310, a feedback can be provided to the sample subject for capturing a new video.

However, in case the signal amplitude for each frame in the determinant window is greater than the threshold signal amplitude ('Yes' branch from block 314), it is indicative of the consistency of the video for determining the physiological parameters. Accordingly, from block 314, the plurality of determinant windows covering a predetermined number of selected frames is chosen from among the determinant windows at block 214.

Figure 4:
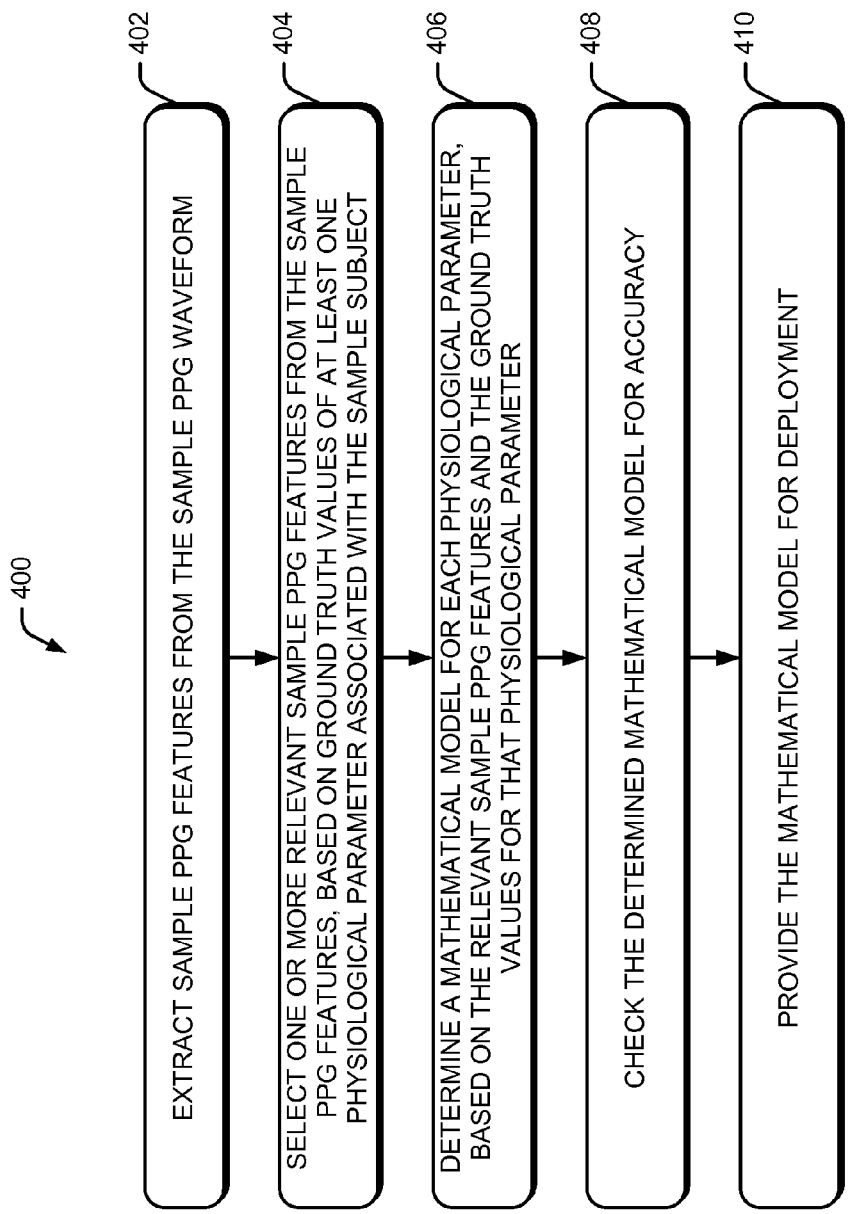
FIG. 4 illustrates a method 400 for determining a mathematical model to monitor physiological parameters associated with a test subject, in accordance with an implementation of the present subject matter.

FIG. 4 illustrates a method 400 for determining a mathematical model to monitor physiological parameters associated with a test subject, in accordance with an implementation of the present subject matter. As will be understood, method 400 continues after block 220 of FIG. 2.

Referring to FIG. 4, at block 402 sample PPG features associated with the sample subject are extracted from the sample PPG waveform obtained at block 220 of FIG. 2. In an example, the sample PPG features can include a set of time domain features or a set of frequency domain features, or both. For instance, the set of time domain features can include a peak-to-peak time interval for the peaking frequencies in the sample PPG waveform, pulse interval, crest time indicative of the time taken for the sample PPG waveform to reach the peaking frequencies, diastolic time, height of the pulse, and area under the sample PPG waveform. In said example, the sample PPG features can be extracted in time domain. In another example, the sample PPG features can be extracted in frequency domain. Alternatively or additionally, physical characteristics associated with the sample subject can be taken into account as the sample PPG features. For instance, the physical characteristics weight of the subject, height of the subject, age of the subject, and other such physical characteristics associated with the sample subject.

At block 404, one or more relevant sample PPG features are selected from the sample PPG features. The relevant PPG features may be selected based on the influence of physiological parameter on the PPG features and vice-versa. In addition, in one example, ground truth values of at least one physiological parameter associated with the sample subject may also be taken into consideration for selecting the relevant sample PPG features. The ground truth values may be understood as actual known values of the physiological parameter to be monitored. In an example in which the physiological parameter is blood pressure, the ground truth values can be values of systolic blood pressure and diastolic blood pressure. In another example in which the physiological parameter being monitored includes ECG features for monitoring heart condition, the ground truth values can be values of the ECG features, such as QRS complex, PR interval, RR interval, and QT interval.

At block 406, a mathematical model for each physiological parameter is determined, based on relevant sample PPG features and the ground truth values for that physiological parameter. The mathematical model is indicative of a correlation between the relevant sample PPG features and the ground truth values. Further, in an example, the mathematical model may be determined using supervised learning techniques. For instance, the supervised learning techniques can include regression-based learning techniques, support vector machine (SVM)-based learning techniques, and artificial neural network (ANN)-based learning techniques.

At block 408, the mathematical model is checked for accuracy, say of estimating and monitoring the physiological parameter. In an example, the mathematical model can be used, in a trial environment, for estimating a physiological parameter bin. The physiological parameter bin indicates a range of values within which the measured value of the physiological parameter lies. The estimated physiological parameter bin can be compared to an actual known value of the physiological parameter to determine whether the mathematical model is accurate or not. In case the mathematical model is not accurate, training of the mathematical model may be achieved to enhance accuracy.

At block 410, the mathematical model is provided for deployment, say at the physiological parameter monitoring device 134, subsequent to passing the accuracy check.

Figure 5:
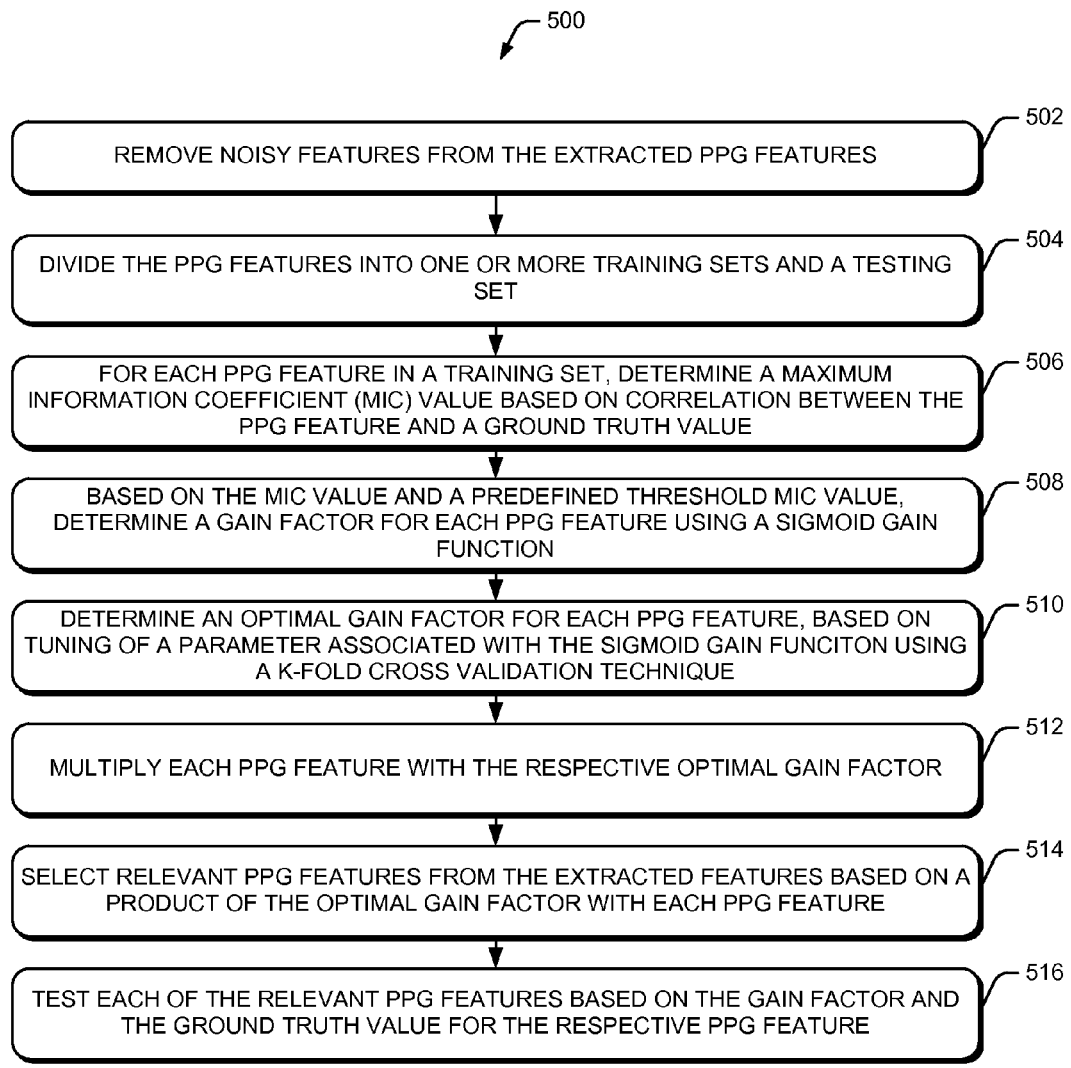
FIG. 5 illustrates a method 500 for selecting relevant sample PPG features from sample PPG features, according to an implementation of the present subject matter.

FIG. 5 illustrates a method 500 for selecting the relevant sample PPG features from the sample PPG features, according to an implementation of the present subject matter. As will be understood, the method 500 explains block 404 of FIG. 4 in detail and is in continuation from block 402 of FIG. 4.

Referring to FIG. 5, at block 502, noisy and incorrect sample PPG features can be removed from the extracted sample PPG features.

At block 504, the entire set of extracted sample PPG features can be divided into one or more training sets and a testing set. In an example, the relevant sample PPG features can be extracted from the training set, whereas the testing set can be used for determining the relevance of the selected sample PPG features and the accuracy of the selection.

At block 506, a correlation coefficient for each of the plurality of sample PPG features in the training set, based on the sample PPG features and the ground truth values. The correlation coefficient can capture a relation between the sample PPG feature and the ground truth value of the physiological parameter. In an example, the correlation coefficient can be a maximum information coefficient (MIC) value and can be determined based on the MIC techniques.

At block 508, a gain factor for each of the plurality of sample PPG features can be determined, based on the correlation coefficient and a gain function. In an example, the gain function can be a sigmoid gain function. Further, the gain factor can be selected based on the selection of a slope constant of the gain function. In said implementation, an optimal value of gain function can be determined based on an optimal value of the slope of the gain function.

At block 510, an optimal gain factor is determined for each sample PPG feature by tuning a parameter associated with the sigmoid gain function determined above. In an example, a k-fold cross validation technique can be employed to determine the optimal gain function. According to said technique, in an example, the training data set can be used to determine the sample PPG features by tuning the value of the slope constant m, i.e., based on different values of the slope constant m, using a classifier model. In an example, the classifier model can be is one of a support vector machine (SVM)-based model and an adaptive neural network (ANN)-based model. In another example, the classifier model can be a regression model.

In said implementation, based on the accuracy of the sample PPG features determined, the value of the gain function can be determined. In said example, the determined sample PPG features can be compared with a known ground truth values to determine the accuracy of determining the sample PPG features. Further, the gain factor for the accurately determined PPG features can be selected as the optimal gain factor. In another example, based on the accurately determined sample PPG features, the optimal value of the slope constant m can be determined. In such a case, based on the optimal value of the slope constant m, the value of the gain factor can be determined from the equation for gain factor Gn.

At block 512, each sample PPG feature is multiplied with the respective optimal gain factor for carrying out selection of the relevant sample PPG features.

At block 514, the relevant sample PPG features can be selected from the extracted features based on a product of the optimal gain factor with each sample PPG feature. In an example, the sample PPG features can be selected based on a threshold value of the gain factor. In another case, the sample PPG features can be selected based on a threshold value of the PPG feature. In both the above cases, when the sample PPG feature is multiplied to the gain factor having a low value, say below the threshold value of the gain factor, the value of the sample PPG feature is suppressed, i.e., falls below the threshold value of the sample PPG feature, and such sample PPG features can be discarded. Accordingly, the sample PPG features for which the value is greater than the threshold value, or for which the value of the gain factor is greater than the threshold value, can be selected as the relevant sample PPG features. In one example, the threshold value of the product of the sample PPG feature with the gain factor can be about 0.001.

At block 516, testing of the selected relevant sample features can be carried out using the testing set, say previously selected from among the extracted sample PPG features, based on the gain factor and the ground truth value. In an implementation, the gain factor selected for each sample PPG feature is employed with the sample PPG features in the testing set for testing whether the sample PPG features selected as relevant based on the gain factor are accurately selected or not. In an example, the sample PPG features in the testing set can be multiplied with the respective gain factors determined for the training set. Based on the multiplication, it can be determined whether the same sample PPG features are selected as the relevant sample PPG features from the testing set, as those selected from the training set.

Figure 6:
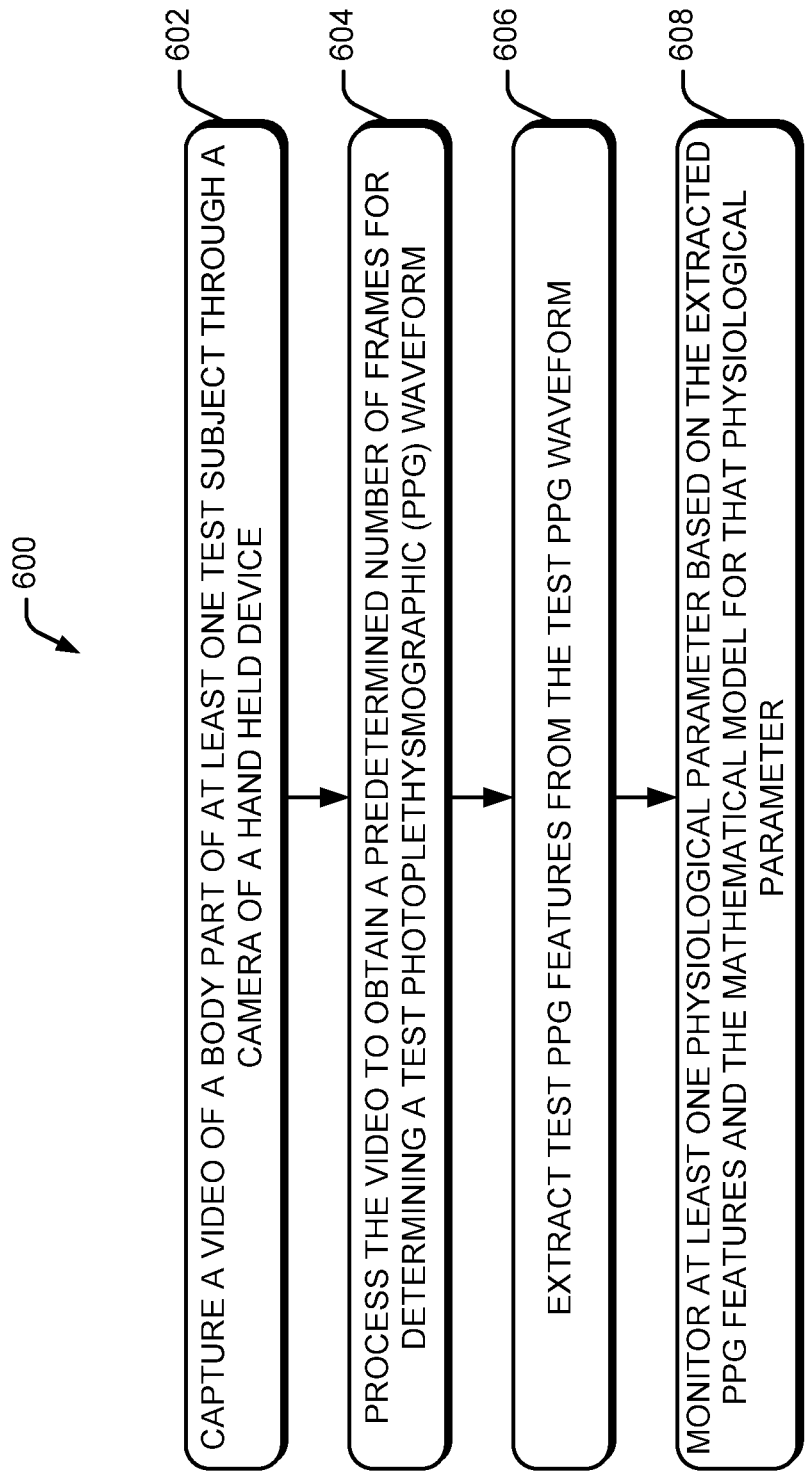
FIG. 6 illustrates a method 600 for monitoring the physiological parameters associated with a test subject, in accordance with an implementation of the present subject matter.

FIG. 6 illustrates a method 600 for monitoring the physiological parameters associated with a test subject using the physiological parameter monitoring device 134, according to an implementation of the present subject matter. As will be understood, method 600 continues after block 410 of FIG. 4.

Referring to FIG. 6, at block 602, a video of body part 140 of at least one test subject is captured through a camera 142 of the physiological parameter monitoring device 134. In an example, the video of a finger tip or an ear lobe can be captured by positioning the finger tip or the ear lobe against a lens of the camera 142 and having the flash light of the camera 142 switched on.

At block 604, the video is processed to determine a test photoplethysmographic (PPG) waveform from the video. In an example, the test PPG waveform is obtained from the video in the same manner as described for obtaining the sample PPG waveform at block 402 and with reference to FIG. 4.

At block 606, relevant test PPG features are extracted from the test PPG waveform. In an example, the relevant test PPG features may be the same as the relevant sample PPG features. In another example, the PPG features corresponding to the relevant sample PPG features may be extracted.

At block 608, at least one of physiological parameter is estimated and monitored based on the extracted relevant test PPG features and the mathematical model corresponding to the at least one physiological parameter. In an example, the physiological parameter bin indicative of the range of values within which the measured value of the physiological parameter lies, can be estimated for the physiological parameter. Therefore, in said example, the estimation done based on the mathematical model can be indicative in nature, instead of being quantitative measurement.

Although implementations for methods and systems for monitoring physiological parameters of a subject using a hand held device are described, it is to be understood that the present subject matter is not necessarily limited to the specific features or methods described. Rather, the specific features and methods are disclosed as implementations for monitoring physiological parameters of a subject using a hand held device.

We claim:

1. A method for monitoring a physiological parameter associated with a subject using a hand held device, the method comprising:

obtaining, by a processor, a plurality of sample photoplethysmographic (PPG) features associated with a sample subject, from a video of a body part of the sample subject;

selecting, by the processor, from among the plurality of sample PPG features, at least one relevant sample PPG feature associated with the physiological parameter, based on a ground truth value of the physiological parameter for the sample subject; and determining, by the processor, based on the at least one relevant sample PPG feature and the ground truth value of the physiological parameter, a mathematical model indicative of a correlation between the at least one relevant sample PPG feature and the physiological parameter, wherein the mathematical model is deployed for monitoring the physiological parameter in real time, wherein the obtaining comprises:

obtaining a plurality of windows from the video, wherein each of the windows includes a predetermined number of frames;

determining at least one quantized colour value for one or more colour models, for each frame in the plurality of windows; and determining consistency of the video by performing consistency analysis for a predetermined number of determinant windows from the plurality of windows, based on the at least one quantized colour value of each frame, wherein the consistency analysis is performed, in response to obtaining the predetermined number of the determinant windows.

2. The method as claimed in claim 1, wherein the obtaining the plurality of sample PPG features comprises extracting the plurality of Sample PPG features from the video in one of a time domain and a frequency domain.

3. The method as claimed in claim 1, wherein the physiological parameter comprises at least one of a blood pressure, an electrocardiograph (ECG) indicative of heart condition, blood oxygen level, and a respiration rate.

4. The method as claimed in claim 1, wherein the plurality of sample PPG features comprise a set of at least one of time domain features and frequency domain features.

5. The method as claimed in claim 1, wherein the plurality of sample PPG features comprise physical characteristics associated with the sample subject.

6. The method as claimed in claim 5, wherein the physical characteristics include height of the sample subject, weight of the sample subject, and age of the sample subject.

7. The method as claimed in claim 1, wherein the determining the mathematical model is based on a supervised learning technique.

8. The method as claimed in claim 1 further comprising:

obtaining test PPG features associated with a test subject from a video of a body part of the test subject; and monitoring the physiological parameter for the test subject, based on the test PPG features and the mathematical model.

9. The method as claimed in claim 1, wherein the selecting comprises:

determining a relevance rating for each of the plurality of sample PPG features, wherein the relevance rating is indicative of a relation of each of the plurality of sample PPG feature with the physiological parameter; and ascertaining the at least one relevant sample PPG feature from among the plurality of sample PPG features, based on the relevance rating of each of the plurality of sample PPG features and a threshold relevance rating.

10. The method as claimed in claim 1, wherein the determining comprises assessing whether the at least one quantized colour value is in a predetermined range of quantized colour values, the consistency analysis being achieved based on the assessing.

11. The method as claimed in claim 1 further comprising:
obtaining, by the processor, from among the determinant windows, a plurality of selected determinant windows covering a predetermined number of frames, in response to the achieving; and
performing, by the processor, a peak frequency detection check for each of the plurality of selected determinant windows, wherein the at least one physiological parameter is ascertained based on the performing.

12. The method as claimed in claim 11, wherein the performing comprises determining a peak frequency of at least one quantized colour value in each of the plurality of selected determinant windows by applying Fast Fourier Transform (FFT) to the at least one quantized colour value of all the frames covered by the plurality of selected determinant.

13. The method as claimed in claim 11 further comprising providing, by the processor, a feedback to the sample subject for capturing a new video, when at least one of the plurality of selected determinant windows fails the peak frequency detection check.

14. The method as claimed in claim 1, wherein the determining the consistency comprises:
determining a position of peak frequency of the at least one quantized colour value for each of the determinant windows;
assessing a frequency drift for peak frequencies across the determinant windows, wherein the frequency drift is indicative of variation in position of peak frequencies across the determinant windows; and
comparing the frequency drift and a threshold frequency drift, wherein the at least one physiological parameter is ascertained in response to the comparing.

15. The method as claimed in claim 1, wherein the determining the consistency comprises:
determining a signal amplitude for the at least one quantized colour value in each frame in the determinant windows; and
comparing the signal amplitude with a threshold signal amplitude, wherein the at least one physiological parameter is ascertained in response to the comparing.

16. The method as claimed in claim 1 further comprising providing, by the processor, a feedback to the sample subject for capturing a new video, when the captured video is inconsistent.

17. The method as claimed in claim 1, wherein the body part is a finger tip of a hand of the sample subject.

18. The method as claimed in claim 1, wherein the selecting comprises:
determining, by the processor, a correlation coefficient for each of the plurality of Sample PPG features, indicative of a relation between a Sample PPG feature and a ground truth value of the physiological parameter;
ascertaining, by the processor, a gain factor for each of the plurality of Sample PPG features, based on the correlation coefficient; and
selecting, by the processor, relevant sample PPG features from among the plurality of Sample PPG features, based on the gain factor, wherein the relevant sample PPG features are deployed for monitoring the physiological parameter in real time.

19. The method as claimed in claim 18, wherein the correlation coefficient is a maximum information coefficient (MIC).

20. The method as claimed in claim 18, wherein the ascertaining the gain factor is based on a sigmoid gain function.

21. The method as claimed in claim 18, wherein the ascertaining the gain factor comprises tuning a slope constant (m) associated with the gain factor, based on accuracy of a k-fold validation technique, the tuning being performed using one of a regression model and a classifier model.

22. The method as claimed in claim 21, wherein the regression model is one of a linear regression model, a non-linear regression model, and a polynomial regression model.

23. The method as claimed in claim 21, wherein the classifier models is one of a support vector machine (SVM)-based model and an adaptive neural network (ANN)-based model.

24. The method as claimed in claim 18, wherein the selecting comprises:
multiplying each of the plurality of Sample PPG features with the respective gain factor; and
selecting the relevant Sample PPG features from among the plurality of Sample PPG features based on a threshold value of each multiplied Sample PPG feature.

25. The method as claimed in claim 18 further comprising ascertaining, by the processor, actual relevance of each of the relevant Sample PPG features based on the respective gain factor.

26. The method as claimed in claim 18, further comprising:
obtaining, by the processor, test PPG features associated with a test subject from a video of a body part of the test subject; and
monitoring, by the processor, the physiological parameter for the test subject, based on the test PPG features and the relevant Sample PPG features.

27. A method for monitoring a physiological parameter associated with a subject using a hand held device, the method comprising:
obtaining a plurality of sample photoplethysmographic (PPG) features associated with a sample subject, from a video of a body part of the sample subject;
selecting, from among the plurality of sample PPG features, at least one relevant sample PPG feature associated with the physiological parameter, based on a ground truth value of the physiological parameter for the subject; and
determining, based on only the at least one relevant sample PPG feature and the ground truth value of the physiological parameter, a mathematical model indicative of a correlation between the relevant sample PPG feature and the physiological parameter, wherein the mathematical model is deployed for monitoring the physiological parameter in real time, the physiological parameter being at least one of a blood pressure (BP) and electrocardiograph (ECG) features,
wherein the selecting comprises:
determining a correlation coefficient for each of the plurality of Sample PPG features, indicative of a relation between a Sample PPG feature and the ground truth value of the physiological parameter;

ascertaining a gain factor for each of the plurality of Sample PPG features, based on the correlation coefficient; and selecting relevant sample PPG features from among the plurality of Sample PPG features, based on the gain factor, wherein the relevant sample PPG features are deployed for monitoring the physiological parameter in real time.

28. A modeling system for monitoring physiological parameters associated with a subject, the modeling system comprising:

a processor;

a processing module coupled to the processor to obtain a plurality of sample photoplethysmographic (PPG) features associated with a sample subject, wherein the sample PPG features are extracted from a video of a body part of the sample subject;

a feature selection module coupled to the processor to select at least one relevant sample PPG features associated with the physiological parameter, from among the plurality of sample PPG features, based on a ground truth value of the physiological parameter; and a modeling module coupled to the processor to determine, based on the at least one relevant sample PPG feature and the ground truth value of the physiological parameter, a mathematical model indicative of a correlation between the relevant sample PPG feature and the physiological parameter, wherein the mathematical model is adapted for monitoring the physiological parameter in real time, wherein the processing module obtains a plurality of windows from the video, wherein each of the windows includes a predetermined number of frames, the modeling system further comprising:

a consistency analysis module coupled to the processor to, determine at least one quantized colour value for one or more colour models, for each frame in the plurality of windows; and determine consistency of the video by performing consistency analysis for a predetermined number of determinant windows from the plurality of windows, based on the at least one quantized colour value of each frame, wherein the consistency analysis is performed in response to obtaining the predetermined number of the determinant windows.

29. The modeling system as claimed in claim 28, wherein the processing module:

obtains the video of the body part of the subject from a sampling device; and processes the video to determine a sample PPG waveform.

30. The modeling system as claimed in claim 28, wherein the processing module obtains the plurality of Sample PPG features from the video in at least one of a time domain and a frequency domain.

31. The modeling system as claimed in claim 28, wherein the modeling module determines the mathematical model based on supervised learning techniques.

32. The modeling system as claimed in claim 28, wherein the feature selection module:

determines a relevance rating for each of the plurality of sample PPG features, wherein the relevance rating is indicative of a relation of each sample PPG feature with the physiological parameter; and compares the relevance rating of each of the plurality of sample PPG features with a threshold relevance rating to select the at least one relevant sample PPG feature.

33. The modeling system as claimed in claim 28, wherein the processing module assesses whether the at least one quantized colour value in a predetermined range of quantized colour values.

34. The modeling system as claimed in claim 33, wherein the consistency analysis module provides a feedback to the subject to capture a new video in response to the assessment by the processing module.

35. The modeling system as claimed in claim 33, wherein the consistency analysis module achieves the consistency analysis in response to the assessment by the processing module.

36. The modeling system as claimed in claim 28, wherein the consistency analysis module:

determines a position of peak frequency of the at least one quantized colour value for each of the determinant windows;

assesses a frequency drift for peak frequencies across the determinant windows, wherein the frequency drift is indicative of variation in position of peak frequencies across the determinant windows; and compares the frequency drift and a threshold frequency drift to determine the at least one physiological parameter in response to the comparison.

37. The modeling system as claimed in claim 28, wherein the consistency analysis module:

determines a signal amplitude for the at least one quantized colour value in each frame in the determinant windows; and compares the signal amplitude with a threshold signal amplitude to ascertain the physiological parameter in response to the comparison.

38. The modeling system as claimed in claim 28, wherein the feature selection module:

determines a correlation coefficient for each of the plurality of Sample PPG features, indicative of a relation between a Sample PPG feature and a ground truth value of the physiological parameter;

ascertains a gain factor for each of the plurality of Sample PPG features, based on the correlation coefficient; and selects the relevant Sample PPG features from among the plurality of Sample PPG features, based on the gain factor, wherein the relevant Sample PPG features are deployed for monitoring the physiological parameter in real time.

39. The modeling system as claimed in claim 38 further comprising a testing module coupled to the processor to ascertaining actual relevance of each of the relevant Sample PPG features based on the respective gain factor.

40. The modeling system as claimed in claim 38, wherein the feature selection module:

multiplies each of the plurality of Sample PPG features with the respective gain factor; and selects the relevant Sample PPG features from among the plurality of Sample PPG features based on a threshold value of each multiplied Sample PPG feature.

41. The modeling system as claimed in claim 38, wherein the correlation coefficient is a maximum information coefficient (MIC).

42. The modeling system as claimed in claim 38, wherein the feature selection module ascertains the gain factor based on a sigmoid gain function.

43. The modeling system as claimed in claim 38, wherein the feature selection module tunes a slope constant (m) associated with the gain factor, based on accuracy of a k-fold validation technique, the tuning being performed using one of a regression model and a classifier model.

44. A physiological parameter monitoring device for monitoring physiological parameters associated with a subject, the physiological parameter monitoring device comprising:
- a processor;
- a monitoring module coupled to the processor to,
  - obtain a mathematical model indicative of a correlation between relevant sample PPG feature and the physiological parameter to be monitored, wherein the relevant sample PPG features are selected from among a plurality of sample PPG features based on influence of the physiological parameter on the plurality of sample PPG features;
  - ascertain test PPG features associated with a test subject from a video of a body part of the test subject, the video being captured using a camera of the physiological parameter monitoring device; and
  - monitor the physiological parameter for the test subject, based on the test PPG features and the mathematical model,
  - wherein the monitoring module:
    - obtains at least one relevant Sample PPG feature having a correlation with a ground truth value of the physiological parameter to be monitored, wherein the relevant sample PPG features are selected from among a plurality of sample PPG features based on a correlation between a Sample PPG feature and a ground truth value of the physiological parameter, and a gain factor determined based on the correlation; and
    - monitors the physiological parameter for the test subject, based on the test PPG features and the relevant PPG features.

45. The physiological parameter monitoring device as claimed in claim 44, wherein the monitoring module provides a feedback to the subject for capturing a new video, when at least one of a video is inconsistent.

46. A non-transitory computer-readable medium comprising instructions executable by a processing resource to:
- obtain a plurality of sample photoplethysmographic (PPG) features associated with a sample subject, from a video of a body part of the sample subject;
- select, from among the plurality of sample PPG features, at least one relevant sample PPG feature associated with the physiological parameter, based on a ground truth value of the physiological parameter for the subject; and
- determine, based on the at least one relevant sample PPG feature and the ground truth value of the physiological parameter, a mathematical model indicative of a correlation between the relevant sample PPG feature and the physiological parameter, wherein the mathematical model is adapted for monitoring the physiological parameter in real time,
- wherein the non-transitory computer-readable medium further comprises instructions executable by the processor to:
  - obtain a plurality of windows from the video, wherein each of the windows includes a predetermined number of frames;
  - determining at least one quantized colour value for one or more colour models, for each frame in the plurality of windows;
  - determining a position of peak frequency of the at least one quantized colour value for each of a predetermined number of determinant windows from the plurality of windows; and
  - performing consistency analysis for the determinant windows, based on the position of peak frequency across the determinant windows.

47. The non-transitory computer readable medium as claimed in claim 46, wherein the non-transitory computer-readable medium further comprises instructions executable by the processor to:
- determine a correlation coefficient for each of the plurality of Sample PPG features, indicative of a relation between a Sample PPG feature and a ground truth value of the physiological parameter;
- ascertain a gain factor for each of the plurality of Sample PPG features, based on the correlation coefficient and a sigmoid gain function; and
- select relevant Sample PPG features from among the plurality of Sample PPG features, based on the gain factor, wherein the relevant Sample PPG features are deployed for monitoring the physiological parameter in real time.

* * * * *